US007749517B2

(12) United States Patent
Young et al.

(10) Patent No.: US 7,749,517 B2
(45) Date of Patent: Jul. 6, 2010

(54) ANTHRAX ANTITOXINS

(75) Inventors: John A. Young, San Diego, CA (US); Heather M. Scobie, San Diego, CA (US); G. Jonah A. Rainey, San Diego, CA (US); Kenneth A. Bradley, Santa Monica, CA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 361 days.

(21) Appl. No.: 11/340,424

(22) Filed: Jan. 26, 2006

(65) Prior Publication Data

US 2007/0172500 A1     Jul. 26, 2007

Related U.S. Application Data

(62) Division of application No. 10/725,946, filed on Dec. 2, 2003, now abandoned.

(60) Provisional application No. 60/431,625, filed on Dec. 5, 2002.

(51) Int. Cl.
*A61K 39/07* (2006.01)
*C07H 21/04* (2006.01)

(52) U.S. Cl. ............................. 424/246.1; 435/252.31; 435/471; 435/69.3; 530/350

(58) Field of Classification Search ................ None
See application file for complete search history.

(56) References Cited

U.S. PATENT DOCUMENTS 6,329,156 B1    12/2001  Cirino et al. ............... 435/7.21
7,074,913 B2 *  7/2006  Young et al. ............... 536/23.7
7,138,417 B2 * 11/2006  Staehle et al. .............. 514/349
2002/0064831 A1 * 5/2002  Davis et al. ................ 435/69.1
2003/0220287 A1 * 11/2003 Phillips et al. ............... 514/44
2003/0221201 A1 * 11/2003 Prior et al. ...................... 800/7
2004/0009182 A1 *  1/2004 Myers et al. ............. 424/184.1
2004/0258699 A1 * 12/2004 Bowdish et al. .......... 424/184.1

(Continued)

FOREIGN PATENT DOCUMENTS

WO          0052022     *   9/2000

(Continued)

OTHER PUBLICATIONS

Lacy, D. Borden et al, PNAS, Apr. 27, 2004, vol. 101(17), pp. 6367-6372, Crystal structure of the von Willebrand factor A domain of human capillary morphogenesis protein 2: An anthrax toxin receptor.*

(Continued)

*Primary Examiner*—Robert B Mondesi
*Assistant Examiner*—Ginny Portner
(74) *Attorney, Agent, or Firm*—Fulbright & Jaworski LLP

(57) ABSTRACT

The present invention provides compositions useful in preparing and/or serving as antitoxins against *Bacillus anthracis*, the causative agent of anthrax. The present invention also provides polypeptides and polynucleotides relating to the capillary morphogenisis gene 2 (CMG-2), vectors containing the polynucleotides and polypeptides, and host cells containing related polynucleotide molecules, all used in association with the treatment of, or the research and development of treatments for anthrax. The present invention also relates to methods for identifying molecules that bind CMG-2 and molecules that reduce the toxicity of anthrax toxin. Finally, the present invention provides methods for treating human and non-human animals suffering from anthrax.

2 Claims, 6 Drawing Sheets

U.S. PATENT DOCUMENTS

| | | | |
|---|---|---|---|
| 2005/0112145 A1* | 5/2005 | Hudson et al. | 424/235.1 |
| 2005/0196407 A1* | 9/2005 | Young et al. | 424/190.1 |
| 2005/0221336 A1* | 10/2005 | Martignetti et al. | 435/6 |
| 2005/0281830 A1* | 12/2005 | Morrow et al. | 424/164.1 |
| 2005/0287149 A1* | 12/2005 | Keler et al. | 424/164.1 |
| 2006/0015969 A1* | 1/2006 | Larrick et al. | 800/288 |
| 2006/0083746 A1* | 4/2006 | Young et al. | 424/164.1 |
| 2006/0110801 A1* | 5/2006 | Young et al. | 435/69.3 |
| 2006/0121045 A1* | 6/2006 | Iverson et al. | 424/164.1 |
| 2006/0246079 A1* | 11/2006 | Morrow et al. | 424/164.1 |
| 2006/0257892 A1* | 11/2006 | Cohen et al. | 435/6 |
| 2006/0258842 A1* | 11/2006 | Groen et al. | 530/350 |
| 2007/0066813 A1* | 3/2007 | Prior et al. | 530/400 |
| 2007/0118934 A1* | 5/2007 | Yu et al. | 800/288 |
| 2008/0299148 A1* | 12/2008 | Young et al. | 424/199.1 |

FOREIGN PATENT DOCUMENTS

| | | |
|---|---|---|
| WO | WO 0052022 | 9/2000 |
| WO | 03/066594 * | 8/2003 |

OTHER PUBLICATIONS

Pannifer, Andrew D. et al, Nature, vol. 414, Nov. 8, 2001, pp. 229-233, Crystal structure of the anthrax lethal factor.*
Wigelsworth, DJ et al, The Journal of Biological Chemistry, vol. 279(22), pp. 23349-23356, May 28, 2004, Binding stoichiometry and Kinetics of the interaction of a human anthrax toxin receptor CMG2, with Protective Antigen.*
Liu, Xiu-Huai et al, The Journal of Biological Chemistry, vol. 276, No. 49, Dec. 7, 2001, pp. 46326-46332, Inhibition of Axotomy-induced Neuronal Apoptosis by Extracellular delivery of a Bcl-XL fusion protein.*
Scobie, HM et al, PNAS, Apr. 29, 2003 (reference of record).*
Friedlander, AM, Nature, Nov. 8, 2001, (refrence of record).*
Bradley, Kenneth A. et al, Identification of the cellular receptor for anthrax toxin, Nature, Nov. 8, 2001, (reference of record).*
Abrami et al., "Anthrax toxin triggers endocytosis of its receptor via a lipid raft-mediated clathrin-dependent process," *J. Cell Biol.*, 160(3):321-328, 2003.
Ahuja et al., "Deletion mutants of protective antigen that inhibit anthrax toxin both in vitro and in vivo," *Biochem. Biophys. Res. Comm.*, 307:446-450, 2003.
Bell et al., "Differential gene expression during capillary morphogenesis in 3D collagen matrices: regulated expression of genes involved in basement membrane matrix assembly, cell cycle progression, cellular differentiation and G-protein signaling," *J. Cell Science*, 113:2755-2773, 2001.
Benson et al., "Identification of residues lining the anthrax protective antigen channel," *Biochem.*, 37:3941-3948, 1998.
Bradley et al., "Identification of the cellular receptor for anthrax toxin," *Nature*, 414:225-229, 2001.
Bradley et al., Binding of anthrax toxin to its receptor is similar to α integrin-ligand interactions, *J. Biol. Chem.*, 278(49):49342-49347, 2003.
Cirino et al., "Disruption of anthrax toxin binding with the use of human antibodies and competitive inhibitors," *Infection and Immunity*, 67(6):2957-2963, 1999.
Cirino et al., "Distruption of anthrax toxin binding with the use of human antibodies and competitive inhibitors," *Infection and Immunity*, 67: 2957-2963, 1999.
Collier and Young, "Anthrax toxin," *Annu. Rev. Cell Dev. Biol.*, 19:45-70, 2003.
Dowling et al., "Mutations in capillary morphogenesis gene-2 result in allelic disorders juvenile hyaline fibromatosis and infantile systemic hyalinosis," *Am. J. Hum. Genet.*, 73(4):957-66, 2003.
Escuyer and Collier, "Anthrax protective antigen interacts with a specific receptor on the surface of CHO-K1 cells," *Infection and Immunity*, 59(10):3381-3386, 1991.
Friedlander, "Tackling anthrax," *Nature*, 414:160-161, 2001.
GenBank Accession No. AK091721, publication date 2004.
GenBank Accession No. AY233452, publication date 2003.
GenBank Accession No. NT_016354, publication date 2006.
Hanks et al., "Mutations in the gene encoding capillary morphogenesis proteins 2 cause juvenile hyaline fibromatosis and infatile systemic hyalinosis," *Am. J. Hum. Genet.*, 73: (4):791-800, 2003.
Leppla et al., "Isolation and characterization of Chinese hamster ovary cell mutants lacking the receptor for anthrax toxin protective antigen," *Zentralblatt Fur Bakteriologie*, $7^{th}$, Suppl 28:119-120, 1996.
Liu and Leppla, "Cell surface tumor endothelium marker 8 cytoplasmic tail-independent anthrax toxin binding, proteolytic processing, oligomer formation, and internalization," *J. Biol. Chem.*, 278(7):5227-5234, 2003.
Maynard et al., "Protection against anthrax toxin by recombinant antibody fragments correlates with antigen affinity," *Nature Biotech.*, 20:597-601, 2002.
Mock and Fouet, "Anthrax," *Annual Rev. Microbiology*, 55:647-671, 2001.
Mourez et al., "2001: a year of major advances in anthrax toxin research," *Trends in Microbiology*, 10(6):287-293, 2002.
Mourez et al., "Designing a polyvalent inhibitor of anthrax toxin," *Nature Biotech.*, 19:958-961, 2001.
Mourez et al., "Mapping dominant-negative mutations of anthrax protective antigen by scanning mutagenesis," *Proc. Natl. Acad. Sci., USA*, 100(24):13803-13808, 2003.
Nada and St. Croix, "Tumor endotheilial markers: new targets for cancer therapy," *Current Opinion in Oncology*, 16:44-49, 2004.
Panchal et al., "Identification of small molecule inhibitors of anthrax lethal factor," *Nature Structural and Molecular Biology*, 11(1):67-72, 2004.
Petosa et al., "Crystal structure of the anthrax toxin protective antigen," *Nature*, 385:833-838, 1997.
Rosovitz et al., "Alanine-scanning mutations in domain 4 of anthrax toxin protective antigen reveal residues important for binding to the cellular receptor and to a neutralizing monoclonal antibody," *J. Biol. Chem.*, 278(33):30936-30944, 2003.
Salazar et al., *Experimental Cell Research*, 249:22-32, 1999.
Scobie et al., "Human capillary morphogenesis protein 2 functions as an anthrax toxin receptor," *Proc. Natl. Acad. Sci., USA*, 100(9):5170-5174, 2003.
Sellman et al., "Dominant-negative mutants of a toxin subunit: an approach to therapy of anthrax," *Science*, 292:695-697, 2001.
Shen et al., "Selective inhibition of anthrax edema factor by adefovir, a drug for chronic hepatitis B virus infection," *Proc. Natl. Acad. Sci., USA*, 101(9):3242-3247, 2004.
Shimaoka et al., "Conformational regulation of integrin structure and function," *Annual Rev. Biophysics Biomolec. Struct.*, 31:486-516, 2002.
Soloihin et al., "Cellular mechanism of anti-anthrax immunity," *Journal of Microbiology, Epidemiology and Immunity*, 5:72-76, 1995.
Tonello et al., "Screening inhibitors of anthrax lethal factor," *Nature*, 418:386, 2002.
Wild et al., "Human antibodies from immunized donors are protective against anthrax toxin in vivo," Nature Biotech., online Oct. 12, 2003.

* cited by examiner

FIG. 1

```
CNG-2 (HS003)          RAFDLYFVLDKSGSVANNMIEIYNFVQQLAEKFVSPEMRLSFIVFSSQATIILPLTUDRGKISKGL
ATR/TM48 (NM_032208)   GGFDLYFILDKSGSVLHNWNKIYYFVEQLABKFISPQLRMSFIVFSTRGTTLMKLTEDREQIRQGL
αM (Shimaoka 2002)     DS-DIAFLIDGSGSIPHDFRRKKEFVSYVMEQLAKSKTLFSLMQYSEKFRIHFTFKEPQHHPHPRS
                          β1              α1            β2      β3         α2

CNG-2 (HS003)          EDLKKVSFVGETIIHEGLKLAKEQIQKAGGLKT---SSIIIALTDGKLDGLVPSYAHKEAKISRSLG
ATR/TM48 (NM_032208)   EKLQKVLPGGDTYMHEGFBRASEQIYYENRQGYRT-ASVIIALTDGRLHEDLFFYSKREAHRSRDLG
αM (Shimaoka 2002)     LVKPITQLLGRTHTATGIRKVVRELFMITHGARKHAFKILVVITDGEKPGDPLGYEDVIPEADREGV
                                α3                        β4                     α4

CNG-2 (HS003)          ASVYCVCVLDFEQAQLERIADSKEQVFPVKGGPQALKGIIHSILAQSCTEILEL
ATR/TM48 (NM_032208)   AIVYCVGVKDFNETQLARIADSKDHVFPVHDGFQALQGIIHSILKKSCIEILAA
αM (Shimaoka 2002)     IR-YVIGVGDAFRSEKSRQELNYIASKPPRDHVFQVNHFEALKTIQHQLREKIP
                          β5          α5           β6           α6
```

FIG. 3

SEQUENCE LISTING

<160> NUMBER OF SEQ ID NOS: 9

<210> SEQ ID NO 1
<211> LENGTH: 1467
<212> TYPE: DNA
<213> ORGANISM: Homo sapiens
<220> FEATURE:
<221> NAME/KEY: CDS
<222> LOCATION: (1)..(1467)

<400> SEQUENCE: 1

```
atg gtg gcg gag cgg tcc ccg gcc cgc agc ccc ggg agc tgg ctg ttc      48
Met Val Ala Glu Arg Ser Pro Ala Arg Ser Pro Gly Ser Trp Leu Phe
 1               5                  10                  15 ccc ggg ctg tgg ctg ttg gtg ctc agc ggt ccc ggg ggg ctg ctg cgc      96
Pro Gly Leu Trp Leu Leu Val Leu Ser Gly Pro Gly Gly Leu Leu Arg
             20                  25                  30 gcc cag gag cag ccc tcc tgc aga aga gcc ttt gat ctc tac ttc gtc     144
Ala Gln Glu Gln Pro Ser Cys Arg Arg Ala Phe Asp Leu Tyr Phe Val
         35                  40                  45 ctg gac aag tct ggg agt gtg gca aat aac tgg att gaa att tat aat     192
Leu Asp Lys Ser Gly Ser Val Ala Asn Asn Trp Ile Glu Ile Tyr Asn
     50                  55                  60 ttc gta cag caa ctt gcg gag aga ttt gtg agc cct gaa atg aga tta     240
Phe Val Gln Gln Leu Ala Glu Arg Phe Val Ser Pro Glu Met Arg Leu
 65                  70                  75                  80 tct ttc att gtg ttt tct tct caa gca act att att ttg cca tta act     288
Ser Phe Ile Val Phe Ser Ser Gln Ala Thr Ile Ile Leu Pro Leu Thr
                 85                  90                  95 gga gac aga ggc aaa atc agt aaa ggc ttg gag gat tta aaa cgt gtt     336
Gly Asp Arg Gly Lys Ile Ser Lys Gly Leu Glu Asp Leu Lys Arg Val
            100                 105                 110 agt cca gta gga gag aca tat atc cat gaa gga cta aag cta gcg aat     384
Ser Pro Val Gly Glu Thr Tyr Ile His Glu Gly Leu Lys Leu Ala Asn
        115                 120                 125 gaa caa att cag aaa gca gga ggc ttg aaa acc tcc agt atc ata att     432
Glu Gln Ile Gln Lys Ala Gly Gly Leu Lys Thr Ser Ser Ile Ile Ile
    130                 135                 140 gct ctg aca gat ggc aag ttg gac ggt ctg gtg cca tca tat gca gag     480
Ala Leu Thr Asp Gly Lys Leu Asp Gly Leu Val Pro Ser Tyr Ala Glu
145                 150                 155                 160 aaa gag gca aag ata tcc agg tca ctt ggg gct agt gtt tat tgt gtt     528
Lys Glu Ala Lys Ile Ser Arg Ser Leu Gly Ala Ser Val Tyr Cys Val
                165                 170                 175 ggt gtc ctt gat ttt gaa caa gca cag ctt gaa aga att gct gat tcc     576
Gly Val Leu Asp Phe Glu Gln Ala Gln Leu Glu Arg Ile Ala Asp Ser
            180                 185                 190 aag gag caa gtt ttc cct gtc aaa ggt gga ttt cag gct ctt aaa gga     624
Lys Glu Gln Val Phe Pro Val Lys Gly Gly Phe Gln Ala Leu Lys Gly
        195                 200                 205 ata att aat tct ata cta gct cag tca tgt act gaa atc cta gaa ttg     672
Ile Ile Asn Ser Ile Leu Ala Gln Ser Cys Thr Glu Ile Leu Glu Leu
```

```
         210                 215                 220
cag ccc tca agt gtc tgt gtg ggg gag gaa ttt cag att gtc tta agt        720
Gln Pro Ser Ser Val Cys Val Gly Glu Glu Phe Gln Ile Val Leu Ser
225                 230                 235                 240 gga aga gga ttc atg ctg ggc agt cgg aat ggc agt gtt ctc tgc act        768
Gly Arg Gly Phe Met Leu Gly Ser Arg Asn Gly Ser Val Leu Cys Thr
                245                 250                 255 tac act gta aat gaa aca tat aca acg agt gta aaa cca gta agt gta        816
Tyr Thr Val Asn Glu Thr Tyr Thr Thr Ser Val Lys Pro Val Ser Val
            260                 265                 270 cag ctt aat tct atg ctt tgt cct gca cct atc ctg aat aaa gct gga        864
Gln Leu Asn Ser Met Leu Cys Pro Ala Pro Ile Leu Asn Lys Ala Gly
        275                 280                 285 gaa act ctt gat gtt tca gtg agc ttt aat gga gga aaa tct gtc att        912
Glu Thr Leu Asp Val Ser Val Ser Phe Asn Gly Gly Lys Ser Val Ile
    290                 295                 300 tca gga tca tta att gtc aca gcc aca gaa tgt tct aac ggg atc gca        960
Ser Gly Ser Leu Ile Val Thr Ala Thr Glu Cys Ser Asn Gly Ile Ala
305                 310                 315                 320 gcc atc att gtt att ttg gtg tta ctg cta ctc ctg ggg atc ggt ttg       1008
Ala Ile Ile Val Ile Leu Val Leu Leu Leu Leu Gly Ile Gly Leu
                325                 330                 335 atg tgg tgg ttt tgg ccc ctt tgc tgc aaa gtg gtt att aag gat cct       1056
Met Trp Trp Phe Trp Pro Leu Cys Cys Lys Val Val Ile Lys Asp Pro
            340                 345                 350 cca cca cca ccc ccc cct gca cca aaa gag gag gaa gaa gaa cct ttg       1104
Pro Pro Pro Pro Pro Pro Ala Pro Lys Glu Glu Glu Glu Glu Pro Leu
        355                 360                 365 cct act aaa aag tgg cca act gtg gat gct tcc tat tat ggt ggt cga       1152
Pro Thr Lys Lys Trp Pro Thr Val Asp Ala Ser Tyr Tyr Gly Gly Arg
    370                 375                 380 ggg gtt gga gga att aaa aga atg gag gtt cgt tgg ggt gat aaa gga       1200
Gly Val Gly Gly Ile Lys Arg Met Glu Val Arg Trp Gly Asp Lys Gly
385                 390                 395                 400 tct act gag gaa ggt gca agg cta gag aaa gcc aaa aat gct gtg gtg       1248
Ser Thr Glu Glu Gly Ala Arg Leu Glu Lys Ala Lys Asn Ala Val Val
                405                 410                 415 aag att cct gaa gaa aca gag gaa ccc atc agg cct aga cca cct cga       1296
Lys Ile Pro Glu Glu Thr Glu Glu Pro Ile Arg Pro Arg Pro Pro Arg
            420                 425                 430 ccc aaa ccc aca cac cag cct cct cag aca aaa tgg tac acc cca att       1344
Pro Lys Pro Thr His Gln Pro Pro Gln Thr Lys Trp Tyr Thr Pro Ile
        435                 440                 445 aag ggt cgt ctt gat gct ctc tgg gct ttg ttg agg cgg cag tat gac       1392
Lys Gly Arg Leu Asp Ala Leu Trp Ala Leu Leu Arg Arg Gln Tyr Asp
    450                 455                 460 cgg gtt tct ttg atg cga cct cag gaa gga gat gag gtt tgt ata tgg       1440
Arg Val Ser Leu Met Arg Pro Gln Glu Gly Asp Glu Val Cys Ile Trp
465                 470                 475                 480 gaa tgt att gag aaa gag cta act gct                                    1467
Glu Cys Ile Glu Lys Glu Leu Thr Ala
                485
```

<210> SEQ ID NO 2
<211> LENGTH: 489
<212> TYPE: PRT
<213> ORGANISM: Homo sapiens

<400> SEQUENCE: 2

Met Val Ala Glu Arg Ser Pro Ala Arg Ser Pro Gly Ser Trp Leu Phe

-continued

```
  1               5                10               15
Pro Gly Leu Trp Leu Val Leu Ser Gly Pro Gly Leu Leu Arg
             20              25              30

Ala Gln Glu Gln Pro Ser Cys Arg Arg Ala Phe Asp Leu Tyr Phe Val
             35              40              45

Leu Asp Lys Ser Gly Ser Val Ala Asn Asn Trp Ile Glu Ile Tyr Asn
             50              55              60

Phe Val Gln Gln Leu Ala Glu Arg Phe Val Ser Pro Glu Met Arg Leu
 65              70              75              80

Ser Phe Ile Val Phe Ser Ser Gln Ala Thr Ile Ile Leu Pro Leu Thr
             85              90              95

Gly Asp Arg Gly Lys Ile Ser Lys Gly Leu Glu Asp Leu Lys Arg Val
            100             105             110

Ser Pro Val Gly Glu Thr Tyr Ile His Glu Gly Leu Lys Leu Ala Asn
            115             120             125

Glu Gln Ile Gln Lys Ala Gly Gly Leu Lys Thr Ser Ser Ile Ile Ile
        130             135             140

Ala Leu Thr Asp Gly Lys Leu Asp Gly Leu Val Pro Ser Tyr Ala Glu
145             150             155             160

Lys Glu Ala Lys Ile Ser Arg Ser Leu Gly Ala Ser Val Tyr Cys Val
                165             170             175

Gly Val Leu Asp Phe Glu Gln Ala Gln Leu Glu Arg Ile Ala Asp Ser
            180             185             190

Lys Glu Gln Val Phe Pro Val Lys Gly Gly Phe Gln Ala Leu Lys Gly
        195             200             205

Ile Ile Asn Ser Ile Leu Ala Gln Ser Cys Thr Glu Ile Leu Glu Leu
        210             215             220

Gln Pro Ser Ser Val Cys Val Gly Glu Glu Phe Gln Ile Val Leu Ser
225             230             235             240

Gly Arg Gly Phe Met Leu Gly Ser Arg Asn Gly Ser Val Leu Cys Thr
                245             250             255

Tyr Thr Val Asn Glu Thr Tyr Thr Thr Ser Val Lys Pro Val Ser Val
            260             265             270

Gln Leu Asn Ser Met Leu Cys Pro Ala Pro Ile Leu Asn Lys Ala Gly
        275             280             285

Glu Thr Leu Asp Val Ser Val Ser Phe Asn Gly Gly Lys Ser Val Ile
        290             295             300

Ser Gly Ser Leu Ile Val Thr Ala Thr Glu Cys Ser Asn Gly Ile Ala
305             310             315             320

Ala Ile Ile Val Ile Leu Val Leu Leu Leu Leu Gly Ile Gly Leu
                325             330             335

Met Trp Trp Phe Trp Pro Leu Cys Cys Lys Val Val Ile Lys Asp Pro
            340             345             350

Pro Pro Pro Pro Pro Ala Pro Lys Glu Glu Glu Glu Pro Leu
        355             360             365

Pro Thr Lys Lys Trp Pro Thr Val Asp Ala Ser Tyr Tyr Gly Gly Arg
    370             375             380

Gly Val Gly Gly Ile Lys Arg Met Glu Val Arg Trp Gly Asp Lys Gly
385             390             395             400

Ser Thr Glu Glu Gly Ala Arg Leu Glu Lys Ala Lys Asn Ala Val Val
            405             410             415

Lys Ile Pro Glu Glu Thr Glu Glu Pro Ile Arg Pro Arg Pro Pro Arg
        420             425             430
```

-continued

```
Pro Lys Pro Thr His Gln Pro Pro Gln Thr Lys Trp Tyr Thr Pro Ile
        435                 440                 445

Lys Gly Arg Leu Asp Ala Leu Trp Ala Leu Leu Arg Arg Gln Tyr Asp
    450                 455                 460

Arg Val Ser Leu Met Arg Pro Gln Glu Gly Asp Glu Val Cys Ile Trp
465                 470                 475                 480

Glu Cys Ile Glu Lys Glu Leu Thr Ala
                485

<210> SEQ ID NO 3
<211> LENGTH: 2234
<212> TYPE: DNA
<213> ORGANISM: Homo sapiens
<220> FEATURE:
<221> NAME/KEY: CDS
<222> LOCATION: (529)..(1992)

<400> SEQUENCE: 3
gttttcggag tgcggaggga gttggggccg ccggaggaga agagtctcca ctcctagttt     60
gttctgccgt cgccgcgtcc cagggacccc ttgtcccgaa gcgcacggca gcggggggaa    120
cttcagccct ccaggcgggg tgggttccag gtccgggtcc gaggcgggcg ctggaggctc    180
ggccccaggc cggagaggaa ctcctttcgc gagctgtcgc cgtgggcccg cattgtctgc    240
aggaactctc cggaatcggg aggggagga ctggatcgcg cttccactgg gattcgtcaa     300
gggttccggc ggcagctgcg gcggtggcgg agactcccct tgtcctctca ggacctccct    360
ctctccctcc ctgtcagctg gtgggtcccg ctgccgcagg cgccggcgtc tcagctgctc    420
gccgcccccc accccagagt gcgtgcaggg tgactcccgc caccctttgcg accctcctga   480 gcttagggga ctgcgagcgg gagggagtct caggcccccg ccgcagg atg gtg gcg      537
                                                   Met Val Ala
                                                     1 gag cgg tcc ccg gcc cgc agc ccc ggg agc tgg ctg ttc ccc ggg ctg     585
Glu Arg Ser Pro Ala Arg Ser Pro Gly Ser Trp Leu Phe Pro Gly Leu
    5                  10                  15 tgg ctg ttg gtg ctc agc ggt ccc ggg ggg ctg ctg cgc gcc cag gag     633
Trp Leu Leu Val Leu Ser Gly Pro Gly Gly Leu Leu Arg Ala Gln Glu
 20                  25                  30                  35 cag ccc tcc tgc aga aga gcc ttt gat ctc tac ttc gtc ctg gac aag     681
Gln Pro Ser Cys Arg Arg Ala Phe Asp Leu Tyr Phe Val Leu Asp Lys
                40                  45                  50 tct ggg agt gtg gca aat aac tgg att gaa att tat aat ttc gta cag     729
Ser Gly Ser Val Ala Asn Asn Trp Ile Glu Ile Tyr Asn Phe Val Gln
             55                  60                  65 caa ctt gcg gag aga ttt gtg agc cct gaa atg aga tta tct ttc att     777
Gln Leu Ala Glu Arg Phe Val Ser Pro Glu Met Arg Leu Ser Phe Ile
         70                  75                  80 gtg ttt tct tct caa gca act att att ttg cca tta act gga gac aga     825
Val Phe Ser Ser Gln Ala Thr Ile Ile Leu Pro Leu Thr Gly Asp Arg
     85                  90                  95 ggc aaa atc agt aaa ggc ttg gag gat tta aaa cgt gtt agt cca gta     873
Gly Lys Ile Ser Lys Gly Leu Glu Asp Leu Lys Arg Val Ser Pro Val
100                 105                 110                 115 gga gag aca tat atc cat gaa gga cta aag cta gcg aat gaa caa att     921
Gly Glu Thr Tyr Ile His Glu Gly Leu Lys Leu Ala Asn Glu Gln Ile
                120                 125                 130 cag aaa gca gga ggc ttg aaa acc tcc agt atc ata att gct ctg aca     969
Gln Lys Ala Gly Gly Leu Lys Thr Ser Ser Ile Ile Ile Ala Leu Thr
            135                 140                 145
```

-continued

```
gat ggc aag ttg gac ggt ctg gtg cca tca tat gca gag aaa gag gca    1017
Asp Gly Lys Leu Asp Gly Leu Val Pro Ser Tyr Ala Glu Lys Glu Ala
        150                 155                 160 aag ata tcc agg tca ctt ggg gct agt gtt tat tgt gtt ggt gtc ctt    1065
Lys Ile Ser Arg Ser Leu Gly Ala Ser Val Tyr Cys Val Gly Val Leu
165                 170                 175 gat ttt gaa caa gca cag ctt gaa aga att gct gat tcc aag gag caa    1113
Asp Phe Glu Gln Ala Gln Leu Glu Arg Ile Ala Asp Ser Lys Glu Gln
180                 185                 190                 195 gtt ttc cct gtc aaa ggt gga ttt cag gct ctt aaa gga ata att aat    1161
Val Phe Pro Val Lys Gly Gly Phe Gln Ala Leu Lys Gly Ile Ile Asn
                200                 205                 210 tct ata cta gct cag tca tgt act gaa atc cta gaa ttg cag ccc tca    1209
Ser Ile Leu Ala Gln Ser Cys Thr Glu Ile Leu Glu Leu Gln Pro Ser
            215                 220                 225 agt gtc tgt gtg ggg gag gaa ttt cag att gtc tta agt gga aga gga    1257
Ser Val Cys Val Gly Glu Glu Phe Gln Ile Val Leu Ser Gly Arg Gly
        230                 235                 240 ttc atg ctg ggc agt cgg aat ggc agt gtt ctc tgc act tac act gta    1305
Phe Met Leu Gly Ser Arg Asn Gly Ser Val Leu Cys Thr Tyr Thr Val
245                 250                 255 aat gaa aca tat aca acg agt gta aaa cca gta agt gta cag ctt aat    1353
Asn Glu Thr Tyr Thr Thr Ser Val Lys Pro Val Ser Val Gln Leu Asn
260                 265                 270                 275 tct atg ctt tgt cct gca cct atc ctg aat aaa gct gga gaa act ctt    1401
Ser Met Leu Cys Pro Ala Pro Ile Leu Asn Lys Ala Gly Glu Thr Leu
                280                 285                 290 gat gtt tca gtg agc ttt aat gga gga aaa tct gtc att tca gga tca    1449
Asp Val Ser Val Ser Phe Asn Gly Gly Lys Ser Val Ile Ser Gly Ser
            295                 300                 305 tta att gtc aca gcc aca gaa tgt tct aac ggg atc gca gcc atc att    1497
Leu Ile Val Thr Ala Thr Glu Cys Ser Asn Gly Ile Ala Ala Ile Ile
        310                 315                 320 gtt att ttg gtg tta ctg cta ctc ctg ggg atc ggt ttg atg tgg tgg    1545
Val Ile Leu Val Leu Leu Leu Leu Leu Gly Ile Gly Leu Met Trp Trp
325                 330                 335 ttt tgg ccc ctt tgc tgc aaa gtg gtt att aag gat cct cca cca cca    1593
Phe Trp Pro Leu Cys Cys Lys Val Val Ile Lys Asp Pro Pro Pro Pro
340                 345                 350                 355 ccc gcc cct gca cca aaa gag gag gaa gaa gaa cct ttg cct act aaa    1641
Pro Ala Pro Ala Pro Lys Glu Glu Glu Glu Pro Leu Pro Thr Lys
                360                 365                 370 aag tgg cca act gtg gat gct gcc tat tat ggt ggt cga ggg gtt gga    1689
Lys Trp Pro Thr Val Asp Ala Ala Tyr Tyr Gly Gly Arg Gly Val Gly
            375                 380                 385 gga att aaa aga atg gag gtt cgt tgg ggt gat aaa gga tct act gag    1737
Gly Ile Lys Arg Met Glu Val Arg Trp Gly Asp Lys Gly Ser Thr Glu
        390                 395                 400 gaa ggt gca agg cta gag aaa gcc aaa aat gct gtg gtg aag att cct    1785
Glu Gly Ala Arg Leu Glu Lys Ala Lys Asn Ala Val Val Lys Ile Pro
405                 410                 415 gaa gaa aca gag gaa ccc atc agg cct aga cca cct cga ccc aaa ccc    1833
Glu Glu Thr Glu Glu Pro Ile Arg Pro Arg Pro Pro Arg Pro Lys Pro
420                 425                 430                 435 aca cac cag cct cct cag aca aaa tgg tac acc cca att aag ggt cgt    1881
Thr His Gln Pro Pro Gln Thr Lys Trp Tyr Thr Pro Ile Lys Gly Arg
                440                 445                 450 ctt gat gct ctc tgg gct ttg ttg agg cgg cag tat gac cgg gtt tct    1929
Leu Asp Ala Leu Trp Ala Leu Leu Arg Arg Gln Tyr Asp Arg Val Ser
```

```
                455                 460                 465
ttg atg cga cct cag gaa gga gat gag ggc cgg tgc ata aac ttc tcc     1977
Leu Met Arg Pro Gln Glu Gly Asp Glu Gly Arg Cys Ile Asn Phe Ser
        470                 475                 480 cga gtt cca tct cag taaaagggaa gcaggaagac caagaaggtc tggcaaagtc     2032
Arg Val Pro Ser Gln
        485 aggctcaggg agactctgcc ctgctgcaga cctcggtgtg gacacacgct gcatagagct   2092 ctccttgaaa acagaggggt ctcaagacat tctgcctacc tattagcttt tctttatttt   2152 tttaactttt tggggggaaa agtatttttg agaagtttgt cttgcaatgt atttataaat   2212 agtaaataaa gttttttacca tt                                          2234

<210> SEQ ID NO 4
<211> LENGTH: 488
<212> TYPE: PRT
<213> ORGANISM: Homo sapiens

<400> SEQUENCE: 4

Met Val Ala Glu Arg Ser Pro Ala Arg Ser Pro Gly Ser Trp Leu Phe
 1               5                  10                  15

Pro Gly Leu Trp Leu Leu Val Leu Ser Gly Pro Gly Gly Leu Leu Arg
            20                  25                  30

Ala Gln Glu Gln Pro Ser Cys Arg Arg Ala Phe Asp Leu Tyr Phe Val
        35                  40                  45

Leu Asp Lys Ser Gly Ser Val Ala Asn Asn Trp Ile Glu Ile Tyr Asn
    50                  55                  60

Phe Val Gln Gln Leu Ala Glu Arg Phe Val Ser Pro Glu Met Arg Leu
65                  70                  75                  80

Ser Phe Ile Val Phe Ser Ser Gln Ala Thr Ile Ile Leu Pro Leu Thr
                85                  90                  95

Gly Asp Arg Gly Lys Ile Ser Lys Gly Leu Glu Asp Leu Lys Arg Val
            100                 105                 110

Ser Pro Val Gly Glu Thr Tyr Ile His Glu Gly Leu Lys Leu Ala Asn
        115                 120                 125

Glu Gln Ile Gln Lys Ala Gly Gly Leu Lys Thr Ser Ser Ile Ile Ile
    130                 135                 140

Ala Leu Thr Asp Gly Lys Leu Asp Gly Leu Val Pro Ser Tyr Ala Glu
145                 150                 155                 160

Lys Glu Ala Lys Ile Ser Arg Ser Leu Gly Ala Ser Val Tyr Cys Val
                165                 170                 175

Gly Val Leu Asp Phe Glu Gln Ala Gln Leu Glu Arg Ile Ala Asp Ser
            180                 185                 190

Lys Glu Gln Val Phe Pro Val Lys Gly Gly Phe Gln Ala Leu Lys Gly
        195                 200                 205

Ile Ile Asn Ser Ile Leu Ala Gln Ser Cys Thr Glu Ile Leu Glu Leu
    210                 215                 220

Gln Pro Ser Ser Val Cys Val Gly Glu Glu Phe Gln Ile Val Leu Ser
225                 230                 235                 240

Gly Arg Gly Phe Met Leu Gly Ser Arg Asn Gly Ser Val Leu Cys Thr
                245                 250                 255

Tyr Thr Val Asn Glu Thr Tyr Thr Thr Ser Val Lys Pro Val Ser Val
            260                 265                 270

Gln Leu Asn Ser Met Leu Cys Pro Ala Pro Ile Leu Asn Lys Ala Gly
        275                 280                 285
```

```
Glu Thr Leu Asp Val Ser Val Ser Phe Asn Gly Gly Lys Ser Val Ile
    290                 295                 300

Ser Gly Ser Leu Ile Val Thr Ala Thr Glu Cys Ser Asn Gly Ile Ala
305                 310                 315                 320

Ala Ile Ile Val Ile Leu Val Leu Leu Leu Leu Leu Gly Ile Gly Leu
                325                 330                 335

Met Trp Trp Phe Trp Pro Leu Cys Cys Lys Val Val Ile Lys Asp Pro
                340                 345                 350

Pro Pro Pro Ala Pro Ala Pro Lys Glu Glu Glu Glu Pro Leu
            355                 360                 365

Pro Thr Lys Lys Trp Pro Thr Val Asp Ala Ser Tyr Tyr Gly Gly Arg
    370                 375                 380

Gly Val Gly Gly Ile Lys Arg Met Glu Val Arg Trp Gly Asp Lys Gly
385                 390                 395                 400

Ser Thr Glu Glu Gly Ala Arg Leu Glu Lys Ala Lys Asn Ala Val Val
                405                 410                 415

Lys Ile Pro Glu Glu Thr Glu Glu Pro Ile Arg Pro Arg Pro Arg
                420                 425                 430

Pro Lys Pro Thr His Gln Pro Gln Thr Lys Trp Tyr Thr Pro Ile
    435                 440                 445

Lys Gly Arg Leu Asp Ala Leu Trp Ala Leu Leu Arg Arg Gln Tyr Asp
    450                 455                 460

Arg Val Ser Leu Met Arg Pro Gln Gly Asp Glu Gly Arg Cys Ile
465                 470                 475                 480

Asn Phe Ser Arg Val Pro Ser Gln
                485

<210> SEQ ID NO 5
<211> LENGTH: 1343
<212> TYPE: DNA
<213> ORGANISM: Artificial
<220> FEATURE:
<223> OTHER INFORMATION: Synthetic primer
<220> FEATURE:
<221> NAME/KEY: CDS
<222> LOCATION: (141)..(1298)

<400> SEQUENCE: 5
cgctgccgca ggcgccggcg tctcagctgc tcgccgcccc ccaccccaga gtgcgtgcag      60
ggtgactccc gccacctttg cgaccctcct gagcttaggg gactgcgagc gggagggagt    120
ctcaggcccc cggccgcagg atg gtg gcg gag cgg tcc ccg gcc cgc agc ccc    173
                        Met Val Ala Glu Arg Ser Pro Ala Arg Ser Pro
                         1               5                  10 ggg agc tgg ctg ttc ccc ggg ctg tgg ctg ttg gtg ctc agc ggt ccc       221
Gly Ser Trp Leu Phe Pro Gly Leu Trp Leu Leu Val Leu Ser Gly Pro
             15                  20                  25 ggg ggg ctg ctg cgc gcc cag gag cag ccc tcc tgc aga aga gcc ttt       269
Gly Gly Leu Leu Arg Ala Gln Glu Gln Pro Ser Cys Arg Arg Ala Phe
         30                  35                  40 gat ctc tac ttc gtc ctg gac aag tct ggg agt gtg gca aat aac tgg       317
Asp Leu Tyr Phe Val Leu Asp Lys Ser Gly Ser Val Ala Asn Asn Trp
     45                  50                  55 att gaa att tat aat ttc gta cag caa ctt gcg gag aga ttt gtg agc       365
Ile Glu Ile Tyr Asn Phe Val Gln Gln Leu Ala Glu Arg Phe Val Ser
 60                  65                  70                  75 cct gaa atg aga tta tct ttc att gtg ttt tct tct caa gca act att       413
Pro Glu Met Arg Leu Ser Phe Ile Val Phe Ser Ser Gln Ala Thr Ile
             80                  85                  90
```

```
                80                  85                  90
att ttg cca tta act gga gac aga ggc aaa atc agt aaa ggc ttg gag    461
Ile Leu Pro Leu Thr Gly Asp Arg Gly Lys Ile Ser Lys Gly Leu Glu
                95                 100                 105 gat tta aaa cgt gtt agt cca gta gga gag aca tat atc cat gaa gga    509
Asp Leu Lys Arg Val Ser Pro Val Gly Glu Thr Tyr Ile His Glu Gly
        110                 115                 120 cta aag cta gcg aat gaa caa att cag aaa gca gga ggc ttg aaa acc    557
Leu Lys Leu Ala Asn Glu Gln Ile Gln Lys Ala Gly Gly Leu Lys Thr
    125                 130                 135 tcc agt atc ata att gct ctg aca gat ggc aag ttg gac ggt ctg gtg    605
Ser Ser Ile Ile Ile Ala Leu Thr Asp Gly Lys Leu Asp Gly Leu Val
140                 145                 150                 155 cca tca tat gca gag aaa gag gca aag ata tcc agg tca ctt ggg gct    653
Pro Ser Tyr Ala Glu Lys Glu Ala Lys Ile Ser Arg Ser Leu Gly Ala
                160                 165                 170 agt gtt tat tgt gtt ggt gtc ctt gat ttt gaa caa gca cag ctt gaa    701
Ser Val Tyr Cys Val Gly Val Leu Asp Phe Glu Gln Ala Gln Leu Glu
        175                 180                 185 aga att gct gat tcc aag gag caa gtt ttc cct gtc aaa ggt gga ttt    749
Arg Ile Ala Asp Ser Lys Glu Gln Val Phe Pro Val Lys Gly Gly Phe
    190                 195                 200 cag gct ctt aaa gga ata att aat tct tct aac ggg atc gca gcc atc    797
Gln Ala Leu Lys Gly Ile Ile Asn Ser Ser Asn Gly Ile Ala Ala Ile
205                 210                 215 att gtt att ttg gtg tta ctg cta ctc ctg ggg atc ggt ttg atg tgg    845
Ile Val Ile Leu Val Leu Leu Leu Leu Leu Gly Ile Gly Leu Met Trp
220                 225                 230                 235 tgg ttt tgg ccc ctt tgc tgc aaa gtg gtt att aag gat cct cca cca    893
Trp Phe Trp Pro Leu Cys Cys Lys Val Val Ile Lys Asp Pro Pro Pro
                240                 245                 250 cca ccc ccc cct gca cca aaa gag gag gaa gaa gaa cct ttg cct act    941
Pro Pro Pro Pro Ala Pro Lys Glu Glu Glu Glu Glu Pro Leu Pro Thr
        255                 260                 265 aaa aag tgg cca act gtg gat gct tcc tat tat ggt ggt cga ggg gtt    989
Lys Lys Trp Pro Thr Val Asp Ala Ser Tyr Tyr Gly Gly Arg Gly Val
    270                 275                 280 gga gga att aaa aga atg gag gtt cgt tgg ggt gat aaa gga tct act   1037
Gly Gly Ile Lys Arg Met Glu Val Arg Trp Gly Asp Lys Gly Ser Thr
285                 290                 295 gag gaa ggt gca agg cta gag aaa gcc aaa aat gct gtg gtg aag att   1085
Glu Glu Gly Ala Arg Leu Glu Lys Ala Lys Asn Ala Val Val Lys Ile
300                 305                 310                 315 cct gaa gaa aca gag gaa ccc atc agg cct aga cca cct cga ccc aaa   1133
Pro Glu Glu Thr Glu Glu Pro Ile Arg Pro Arg Pro Pro Arg Pro Lys
                320                 325                 330 ccc aca cac cag cct cct cag aca aaa tgg tac acc cca att aag ggt   1181
Pro Thr His Gln Pro Pro Gln Thr Lys Trp Tyr Thr Pro Ile Lys Gly
        335                 340                 345 cgt ctt gat gct ctc tgg gct ttg ttg agg cgg cag tat gac cgg gtt   1229
Arg Leu Asp Ala Leu Trp Ala Leu Leu Arg Arg Gln Tyr Asp Arg Val
    350                 355                 360 tct ttg atg cga cct cag gaa gga gat gag gtt tgt ata tgg gaa tgt   1277
Ser Leu Met Arg Pro Gln Glu Gly Asp Glu Val Cys Ile Trp Glu Cys
365                 370                 375 att gag aaa gag cta act gct tgagtcagta taatggaggc agggaaatag       1328
Ile Glu Lys Glu Leu Thr Ala
380                 385 taataaaaaa tgatt                                                   1343
```

<210> SEQ ID NO 6
<211> LENGTH: 386
<212> TYPE: PRT
<213> ORGANISM: Artificial
<220> FEATURE:
<223> OTHER INFORMATION: Synthetic peptide

<400> SEQUENCE: 6

```
Met Val Ala Glu Arg Ser Pro Ala Arg Ser Pro Gly Ser Trp Leu Phe
  1               5                  10                  15

Pro Gly Leu Trp Leu Leu Val Leu Ser Gly Pro Gly Gly Leu Leu Arg
                 20                  25                  30

Ala Gln Glu Gln Pro Ser Cys Arg Arg Ala Phe Asp Leu Tyr Phe Val
             35                  40                  45

Leu Asp Lys Ser Gly Ser Val Ala Asn Asn Trp Ile Glu Ile Tyr Asn
 50                  55                  60

Phe Val Gln Gln Leu Ala Glu Arg Phe Val Ser Pro Glu Met Arg Leu
 65                  70                  75                  80

Ser Phe Ile Val Phe Ser Ser Gln Ala Thr Ile Ile Leu Pro Leu Thr
                 85                  90                  95

Gly Asp Arg Gly Lys Ile Ser Lys Gly Leu Glu Asp Leu Lys Arg Val
                100                 105                 110

Ser Pro Val Gly Glu Thr Tyr Ile His Glu Gly Leu Lys Leu Ala Asn
            115                 120                 125

Glu Gln Ile Gln Lys Ala Gly Gly Leu Lys Thr Ser Ser Ile Ile Ile
130                 135                 140

Ala Leu Thr Asp Gly Lys Leu Asp Gly Leu Val Pro Ser Tyr Ala Glu
145                 150                 155                 160

Lys Glu Ala Lys Ile Ser Arg Ser Leu Gly Ala Ser Val Tyr Cys Val
                165                 170                 175

Gly Val Leu Asp Phe Glu Gln Ala Gln Leu Glu Arg Ile Ala Asp Ser
            180                 185                 190

Lys Glu Gln Val Phe Pro Val Lys Gly Gly Phe Gln Ala Leu Lys Gly
        195                 200                 205

Ile Ile Asn Ser Ser Asn Gly Ile Ala Ala Ile Ile Val Ile Leu Val
210                 215                 220

Leu Leu Leu Leu Leu Gly Ile Gly Leu Met Trp Trp Phe Trp Pro Leu
225                 230                 235                 240

Cys Cys Lys Val Val Ile Lys Asp Pro Pro Pro Pro Pro Pro Pro Ala
                245                 250                 255

Pro Lys Glu Glu Glu Glu Glu Pro Leu Pro Thr Lys Lys Trp Pro Thr
            260                 265                 270

Val Asp Ala Ser Tyr Tyr Gly Gly Arg Gly Val Gly Gly Ile Lys Arg
        275                 280                 285

Met Glu Val Arg Trp Gly Asp Lys Gly Ser Thr Glu Glu Gly Ala Arg
    290                 295                 300

Leu Glu Lys Ala Lys Asn Ala Val Val Lys Ile Pro Glu Glu Thr Glu
305                 310                 315                 320

Glu Pro Ile Arg Pro Arg Pro Arg Pro Lys Pro Thr His Gln Pro
                325                 330                 335

Pro Gln Thr Lys Trp Tyr Thr Pro Ile Lys Gly Arg Leu Asp Ala Leu
            340                 345                 350

Trp Ala Leu Leu Arg Arg Gln Tyr Asp Arg Val Ser Leu Met Arg Pro
        355                 360                 365
```

```
Gln Glu Gly Asp Glu Val Cys Ile Trp Glu Cys Ile Glu Lys Glu Leu
    370                 375                 380

Thr Ala
385

<210> SEQ ID NO 7
<211> LENGTH: 184
<212> TYPE: PRT
<213> ORGANISM: Artificial
<220> FEATURE:
<223> OTHER INFORMATION: Synthetic peptide

<400> SEQUENCE: 7

Arg Ala Phe Asp Leu Tyr Phe Val Leu Asp Lys Ser Gly Ser Val Ala
  1               5                  10                  15

Asn Glu Trp Ile Glu Ile Tyr Asn Phe Val Gln Gln Leu Ala Glu Arg
             20                  25                  30

Phe Val Ser Pro Glu Met Arg Leu Ser Phe Ile Val Phe Ser Ser Gln
         35                  40                  45

Ala Thr Ile Ile Leu Pro Leu Thr Gly Asp Arg Gly Lys Ile Ser Lys
     50                  55                  60

Gly Leu Glu Asp Leu Lys Lys Val Ser Pro Val Gly Glu Thr Tyr Ile
 65                  70                  75                  80

His Glu Gly Leu Lys Leu Ala Asn Glu Gln Ile Gln Lys Ala Gly Gly
                 85                  90                  95

Leu Ala Thr Ser Ser Ile Ile Ala Leu Thr Asp Gly Lys Leu Asp
                100                 105                 110

Gly Leu Val Pro Ser Tyr Ala Glu Lys Glu Ala Lys Ile Ser Arg Ser
            115                 120                 125

Leu Gly Ala Ser Val Tyr Cys Val Gly Val Leu Asp Phe Glu Gln Ala
        130                 135                 140

Gln Leu Glu Arg Ile Ala Asp Ser Lys Glu Gln Val Phe Pro Val Leu
145                 150                 155                 160

Gly Gly Pro Gln Ala Leu Lys Gly Ile Ile Asn Ser Ile Leu Ala Gln
                165                 170                 175

Ser Cys Thr Glu Ile Leu Glu Leu
            180

<210> SEQ ID NO 8
<211> LENGTH: 186
<212> TYPE: PRT
<213> ORGANISM: Artificial
<220> FEATURE:
<223> OTHER INFORMATION: Synthetic peptide

<400> SEQUENCE: 8

Gly Gly Phe Asp Leu Tyr Phe Ile Leu Asp Lys Ser Gly Ser Val Leu
  1               5                  10                  15

His Glu Trp Asn Glu Ile Tyr Tyr Phe Val Glu Gln Leu Ala His Lys
             20                  25                  30

Phe Ile Ser Pro Gln Leu Arg Met Ser Phe Ile Val Phe Ser Thr Arg
         35                  40                  45

Gly Thr Thr Leu Met Lys Leu Thr Glu Asp Arg Glu Gln Ile Arg Gln
     50                  55                  60

Gly Leu Glu Lys Leu Gln Lys Val Leu Pro Gly Gly Asp Thr Tyr Asn
 65                  70                  75                  80

His Glu Gly Phe Ser Arg Ala Ser Glu Gln Ile Tyr Tyr Glu Asn Arg
```

```
                     85                  90                  95
Gln Gly Tyr Arg Thr Ala Ser Val Ile Ile Ala Leu Thr Asp Gly Glu
                100                 105                 110
Leu His Glu Asp Leu Phe Phe Tyr Ser Lys Arg Glu Ala Asn Arg Ser
            115                 120                 125
Arg Asp Leu Gly Ala Ile Val Ile Cys Val Gly Val Lys Asp Phe Asn
        130                 135                 140
Glu Thr Gln Leu Ala Arg Ile Ala Asp Ser Lys Asp His Val Phe Pro
145                 150                 155                 160
Val Asn Asp Gly Phe Gln Ala Leu Gln Gly Ile Ile Asn Ser Ile Leu
                165                 170                 175
Lys Lys Ser Cys Ile Glu Ile Leu Ala Ala
                180                 185

<210> SEQ ID NO 9
<211> LENGTH: 186
<212> TYPE: PRT
<213> ORGANISM: Artificial
<220> FEATURE:
<223> OTHER INFORMATION: Synthetic peptide

<400> SEQUENCE: 9

Asp Ser Asp Ile Ala Phe Leu Ile Asp Gly Ser Gly Ser Ile Pro His
1               5                   10                  15
Asp Phe Arg Arg Met Lys Glu Phe Val Ser Thr Val Met Glu Gln Leu
                20                  25                  30
Lys Lys Ser Lys Thr Leu Phe Ser Leu Met Gln Tyr Ser Glu Lys Phe
            35                  40                  45
Arg Ile His Phe Thr Phe Lys Glu Phe Gln Asn Asn Pro Asn Pro Arg
        50                  55                  60
Ser Leu Val Lys Pro Ile Thr Gln Leu Leu Gly Arg Thr Glu Thr Ala
65                  70                  75                  80
Thr Gly Ile Arg Lys Val Val Arg Glu Leu Phe Trp Ile Thr Asn Gly
                85                  90                  95
Ala Arg Lys Asn Ala Pro Phe Lys Ile Leu Val Val Ile Thr Asp Gly
                100                 105                 110
Glu Lys Phe Gly Asp Pro Leu Gly Tyr Glu Asp Val Ile Pro Glu Ala
            115                 120                 125
Asp Arg Glu Gly Val Ile Arg Tyr Val Ile Gly Val Gly Asp Ala Phe
        130                 135                 140
Arg Ser Glu Lys Ser Arg Gln Glu Leu Asn Thr Ile Ala Ser Lys Pro
145                 150                 155                 160
Pro Arg Asp His Val Phe Gln Val Asn Asn Phe Glu Ala Leu Lys Thr
                165                 170                 175
Ile Gln Asn Gln Leu Arg Glu Lys Ile Phe
                180                 185
```

ANTHRAX ANTITOXINS

This application is a divisional application of U.S. application Ser. No. 10/725,946, filed Dec. 2, 2003, which claims the benefit of U.S. Provisional Application No. 60/431,625, filed Dec. 5, 2002. The entire text of the above provisional application is specifically incorporated by reference.

This invention was made with government support under grant number AI48489 awarded by the National Institutes of Health. The government has certain rights in the invention.

BACKGROUND OF THE INVENTION

A. Field of Invention

The present invention provides compositions that are useful in preparing and/or serving as antitoxins against the gram-positive bacterium Bacillus anthracis, the causative agent of anthrax.

B. Related Art

*B. anthracis* has three major routes by which its spores infect mammalian hosts. One route is through cuts or abrasions of the skin, which leads to the generally benign and self-limiting cutaneous form of the disease. The second is through spore ingestion, which generally results in gastrointestinal anthrax. The third is by inhalation of the spores into the lungs, causing inhalational anthrax.

Inhalational anthrax is the deadliest form of the disease. After it is inhaled, the anthrax spores migrate to and germinate within alveolar macrophages that are then trafficked to lymph nodes where the bacterium is able to grow and gain access to the bloodstream. Once in the bloodstream, a serious systemic form of anthrax develops, rapidly leading to death in a high percentage (up to 80%) of cases (Inglesby et al., 2002). As a result, anthrax is listed by the Centers for Disease Control and Prevention as one of six category A agents considered likely to have the most adverse public health impact if used in a biological attack.

Highly virulent forms of *B. anthracis* encode two types of virulence factors: a poly-D-glutamic acid capsule that protects the bacterium against phagocytosis, and two known anthrax toxins, lethal toxin (LeTx) and edema toxin (EdTx) (Mock and Fouet, 2001). Both LeTx and EdTx are secreted from the bacterium and believed to be primarily responsible for the major symptoms and death associated with anthrax. The toxins are binary, AB-type toxins, consisting of a shared B-moiety (designated a protective antigen or PA) and either of two A-moieties, designated as lethal factor (LF) for LeTX and edema factor (EF) for EdTx. EF is a calcium/calmodulin-dependent adenylate cyclase that causes edema at the site of infection as well as elevated levels of cAMP, thus interfering with bacterial phagocytosis in neutrophils and contributing to bacterial multiplication in the host. LF is a zinc-dependent protease capable of inducing macrophage lysis as well as the cleaving and inactivation of members of the mitogen activated protein kinase kinase protein family (MAPKK). LeTx is also thought to contribute to anthrax pathogenesis by causing macrophages to release pro-inflammatory cytokines and reactive oxygen intermediates believed to cause death by a shock-like syndrome. The precise cause of death by anthrax, however, remains to be established.

The protective antigen (PA) is initially synthesized as an 83 kDa protein that binds specifically, reversibly, and with a high degree of affinity (Kd ~1 nM) to a receptor on the surface of the host cells. Once bound, the PA is cleaved into two protein fragments by a member of the furin family of proteases. As illustrated in FIG. 1, the N-terminal $PA_{20}$ fragment is removed and the C-terminal $PA_{63}$ fragment remains associated with the receptor. $PA_{63}$ then spontaneously self-associates with other $PA_{63}$ fragments at the cell surface to form heptameric ring-shaped oligomers that can each bind up to three molecules of either LF or EF. (Mogridge et al., 2002; Cunningham et al., 2002).

The assembled anthrax toxin complexes are then taken up into cells by receptor-mediated endocytosis and are trafficked to an acidic intracellular compartment. At this location, the $PA_{63}$ heptamer (the prepore) undergoes a dramatic conformational change under the influence of low pH resulting in the formation of a 14-strand transmembrane β-barrel (Petosa et al., 1997; Benson et al., 1998). Concomitantly, EF and LF are translocated across the membrane to the cytosol, an event that is thought to be mediated by the membrane-associated PA pore.

Recent studies have led to the identification of the Anthrax Toxin Receptor (ATR) as a cellular receptor for PA (Bradley et al., 2001). ATR is a type 1 membrane protein with an extracellular von Willebrand factor type A-domain (or integrin-related I-domain) that binds directly to PA, and has been shown to be from the same cellular gene as TEM8 (Tumor Endothelial Marker 8), a ubiquitously expressed gene known to be specifically upregulated in tumor vasculature. To date, three differently spliced mRNAs derived from this gene have been described and designated as TEM8 splice variants 1, 2 (ATR), and 3. The first two splice variants encode transmembrane receptors with different cytoplasmic tails. Each of these proteins can serve as a receptor for anthrax toxin. The third splice variant encodes a protein believed to be secreted from cells as it lacks any obvious transmembrane or other membrane attachment sequence and appears not to mediate anthrax toxin entry.

Due to the high mortality rate associated with inhalational anthrax, there is much interest in developing effective anthrax vaccines. An anthrax vaccine (AVA) representing a sterile supernatant from an attenuated strain of the bacterium is currently licensed for use in the USA. The major protective component of this vaccine is PA (Friedlander et al., 1999). Although the Institute of Medicine has concluded that this vaccine is as safe as others for human administration, it suffers from several major drawbacks, including an 18-month immunization schedule, the need for annual booster doses, and associated symptoms such as headaches, chills, malaise and muscle aches (Vastag, 2002). It may also be possible for bioterrorists to engineer PA in such a way as to alter its antigenic epitopes without changing its function, thereby rendering this vaccine ineffective.

Antibiotics such as doxycycline, penicillin, and ciprofloxacin can also be effective at preventing death by preventing bacterial multiplication (Inglesby, 2002). However, two major drawbacks are inherent in relying solely upon antibiotic therapy. First, antibiotics are effective only if administered early after infection, presumably at a time when fatal levels of toxin have not yet accumulated in the bloodstream. Second, drugs are likely to be ineffective against any organisms engineered to be antibiotic-resistant.

In response to this latter concern, a new approach has been developed to inhibit bacterial multiplication using the PlyG lysin derived from the γ-bacteriophage of *B. anthracis* to degrade bacterial cell wall components (Schuch et al., 2002). While this approach holds much promise for dealing with the threat of antibiotic-resistant bacteria, it suffers from the same limitation as the use of antibiotics, namely that it would have to be administered early during the course of infection to be effective.

Another approach is to develop antitoxins that can eliminate and/or inactivate anthrax toxins. Currently, four different types of anthrax antitoxin have been described: PA-specific antibodies; soluble receptor-based antitoxins; polyvalent inhibitors (PV1); and dominant-negative forms of PA (DN-PA).

PA-specific antibodies prevent PA binding to its receptor. Recently, high-affinity single-chain variable PA-specific antibody fragments have also been shown to be effective at protecting rats against lethal toxin challenge (Maynard et al., 2002). Such antibodies could prove useful in treating infections by common strains of B. anthracis; however, they would most likely be ineffective against bacteria engineered to express an antigenically-altered form of PA.

Recent studies have also used phage display to identify a dodecapeptide capable of blocking EF/LF binding to the PA heptameric ring (Mourez et al., 2001). In these studies, the multivalent display of this peptide, by covalent attachment to a polyacrylamide backbone (PVI), dramatically increased its inhibitory activity and effectively prevented death of rats challenged with LeTx. Although encouraging, this system is not well suited for multivalent peptide display in humans as acrylamide is highly toxic.

Recent studies involving DN-PA have also described altered forms of PA which harbor amino acid changes that abrogate translocation of anthrax toxin A-moieties into cytoplasm, without affecting their ability to bind to cell surface associated $PA_{63}$. These mutant forms of PA are also capable of blocking EF/LF translocation by wild-type PA when they are co-assembled into heptameric rings at the cell surface (Sellman et al., 2001). Presently, this is the most promising class of anthrax antitoxin, especially when one considers the fact that this reagent may also serve as an effective PA-based vaccine.

Finally, soluble forms of ATR have been recently developed to serve as soluble receptor-based antitoxins. In practice, the soluble ATR acts as a "decoy" to compete for and to prevent PA-receptor binding. Studies have shown that such ATR decoys are able to protect cells in culture from being killed by recombinant anthrax toxin (Bradley et al., 2001) and to protect rats against a lethal toxin challenge. Although ATR decoys should be effective inhibitors of anthrax toxin when administered in vivo, they may cause adverse side-effects because they contain the presumed sites of physiological ligand-interaction, and therefore may disrupt critical ligand-receptor interactions in the host.

It is clear that it is not yet known which, if any, of the above antitoxins (or combinations thereof) will be effective at eliminating the risk posed by exposure to high systemic levels of anthrax toxin in the bloodstream. This is of particular concern when one considers the use of engineered organisms in a biological attack. Thus, it seems prudent to further develop additional antitoxins or a "cocktail" of antitoxins that, when used together, will be far more effective than would any one alone. It would also seem prudent to develop additional antitoxins capable of inhibiting anthrax toxin activity while not having a deleterious effect on the host.

SUMMARY OF THE INVENTION

The present invention is summarized as novel compositions useful as antitoxins against B. anthracis, the causative agent of anthrax, and methods for making the same. In general, the antitoxin is able to inhibit the interaction between the protective antigen (PA) of B. anthracis and its receptors. The invention employs isolated polypeptides and polynucleotides relating to the capillary morphogenisis gene 2 (CMG-2), vectors containing the polynucleotides and polypeptides, and host cells containing related polynucleotide molecules. The invention also relates to methods for identifying molecules that bind CMG-2 and molecules that reduce the toxicity of anthrax toxin.

The present application discloses that polypeptides of the CMG-2 protein, and fragments thereof, are able to bind to, inhibit and affect PA activity. The complete CMG-2 protein includes a putative signal peptide (SP), an integrin-like inserted domain (I-domain) and a type I transmembrane (TM) domain. PA binds to CMG-2 at its I-domain along a metal ion-dependent adhesion site (MIDAS), comprised of five amino acid residues (DXSXS ... T ... D; where X can be any amino acid).

In one aspect, the invention is summarized in that an alternative anthrax toxin receptor is identified to be a polypeptide having an amino acid sequence selected from SEQ ID NO:2, SEQ ID NO:4, SEQ ID NO: 6, a PA-binding fragment of any of the foregoing, and a PA-binding variant of any of the foregoing polypeptides having conservative or non-conservative amino acid substitutions or other changes relative to the disclosed sequences.

In a related aspect, the invention further relates to the use of an isolated polynucleotide that encodes any of the above-mentioned polypeptides and their complements, and a polynucleotide that hybridizes under moderately stringent or stringent hybridization conditions to any of the foregoing, for the development or use as an agent against anthrax toxins.

In still another related aspect, the invention encompasses the use of a cloning vector and an expression vector comprising any of the foregoing polynucleotides, whether or not the polynucleotide is operably linked to an expression control sequence that does not natively promote transcription or translation of the polynucleotide, for the development or use as an agent against anthrax toxins.

By identifying the polypeptides and polynucleotides of the invention, the applicant enables the skilled artisan to detect and quantify MRNA and CMG-2 protein in a sample, and to generate CMG-2 transgenic and CMG-2 knock-out animals using methods available to the art.

Further, the invention includes a host cell comprising any such vector in its interior. Also within the scope of the present invention is a host cell having a polynucleotide of the invention integrated into the host cell genome at a location that is not the native location of the polynucleotide.

In yet another aspect, the invention is a method for producing an anthrax toxin receptor polypeptide that includes the steps of transcribing a polynucleotide that encodes a PA-binding polypeptide, operably linked to an upstream expression control sequence, to produce an mRNA for the PA-binding polypeptide, and translating the mRNA to produce the PA-binding polypeptide. This method can be performed in a host cell when the polynucleotide is operably linked to the expression control sequence in an expression vector, and wherein the expression vector is delivered into a host cell, the expression control sequence being operable in the host cell. Alternatively, at least one of the transcribing and translating steps can be performed in an in vitro system, examples of which are well known in the art and commercially available. In either case, the polypeptide can be isolated from other cellular material using readily available methods.

In still another aspect, the invention is a method for identifying an agent that can alter the effect of anthrax toxin on the host cell or organism. The method includes the steps of separately exposing a plurality of putative agents in the presence of anthrax toxin to a plurality of cells having on their surface at least a portion of CMG-2 that binds to PA or a component thereof, comparing the effect of anthrax toxin on the cells in the presence and absence of the agent, and identifying at least one agent that alters an effect of anthrax toxin on the cells. In a related aspect, the present invention encompasses an agent that alters binding of PA to CMG-2 and/or other anthrax toxin receptors, such as ATR.

The present invention also encompasses a method for reducing or preventing anthrax toxin-related damage in vivo or in vitro to human or non-human cells having an ATR or CMG-2 receptor on an outer cell surface, the method comprising the step of exposing the cells to a CMG-2 derived agent that reduces binding of anthrax to ATR, CMG-2 or other anthrax toxin receptors. Similarly, the invention relates to a method for reducing or preventing damage in vivo or in vitro to human or non-human cells caused by anthrax toxin by exposing PA to an agent that reduces binding of PA to ATR, CMG-2 or other anthrax toxin receptors.

The present invention is also a method for identifying a mutant of the extracellular CMG-2 domain or fragment thereof having altered (increased or reduced) binding affinity for PA.

It is an object of the invention to identify polypeptides that encode a mammalian CMG-2 anthrax receptor, as well as fragments, mutants, and variants thereof and polynucleotides encoding the same. Other objects, advantages and features of the invention will become apparent from the following specifications and claims.

BRIEF DESCRIPTION OF THE DRAWINGS

Figure 1:
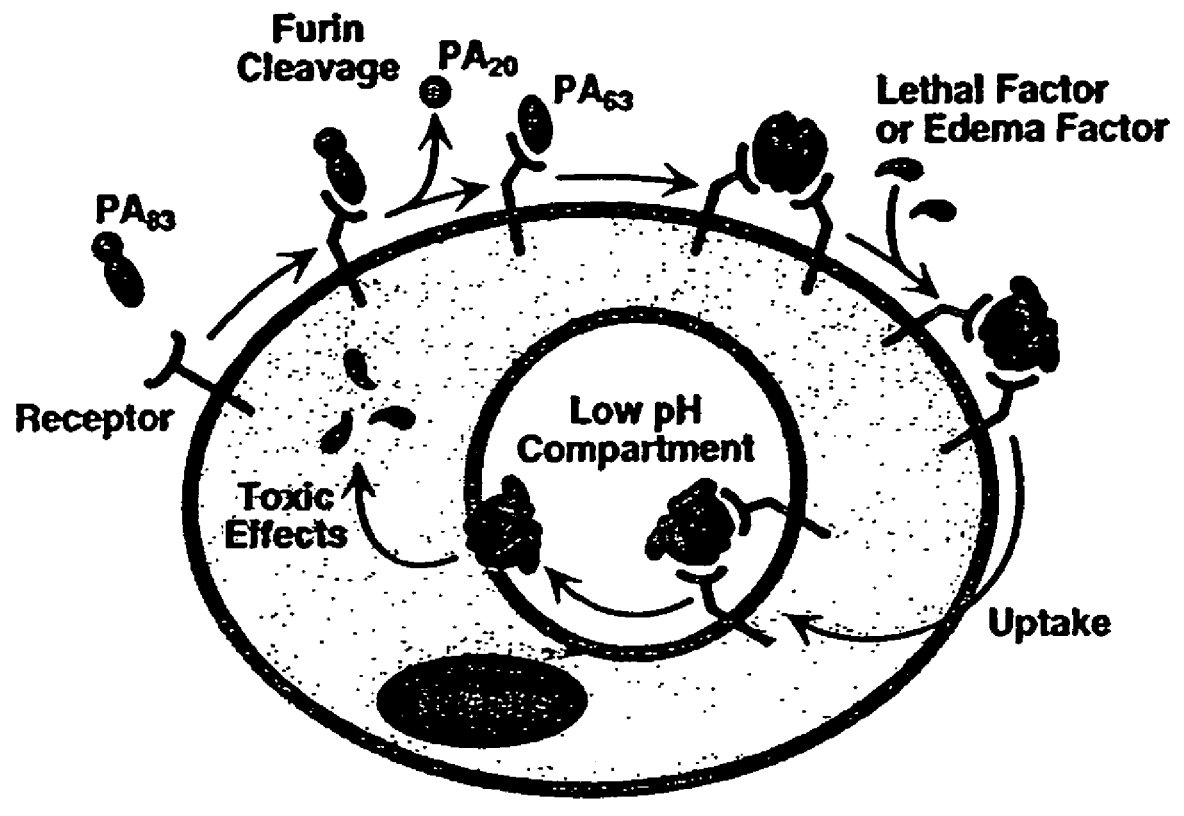

FIG. 1—An illustration of the uptake pathway of anthrax toxins into cells.

FIG. 3—An alignment of the ATR, CMG-2 and aM integrin 1-domains (SEQ ID NOS:7, 8 and 9).

DETAILED DESCRIPTION OF THE INVENTION

The present invention provides compositions useful in preparing or serving as an antitoxin against B. anthracis, the causative agent of anthrax. Such compositions include complete and/or partial isolated polypeptides of the capillary morphogenesis gene 2 (CMG-2) protein, and isolated polynucleotides encoding such polypeptides.

The applicants have identified the CMG-2 protein as a second protein capable of binding to the B. anthracis protective antigen (PA). The CMG-2 protein is closely related (40% identity) to the anthrax toxin receptor (ATR) previously identified as a surface cell receptor used by PA to bind and internalize the anthrax toxins, thus contributing to the pathogenesis of B. anthracis. Like ATR, CMG-2 binds PA on the cell surface and supports toxin entry. Unlike ATR, which is upregulated in tumor vasculature, CMG-2 expression is dramatically upregulated in cultured human umbilical vein endothelial cells (HUVEs) induced to undergo in vitro capillary morphogenesis.

Figure 2:
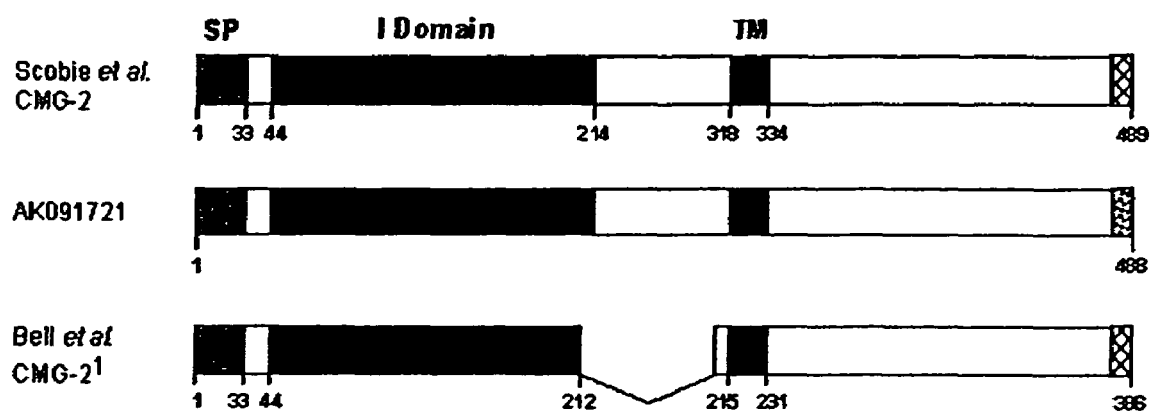
FIG. 2—A comparison of the major components of SEQ ID NOS: 2, 4 and 6.

The CMG-2 protein is encoded by capillary morphogenesis gene 2, and has been previously shown to bind specifically to laminin and collagen type IV (Bell et al., 2001). Presented here as SEQ ID NO:1 is a cDNA clone isolated and determined by the applicants. The isolated cDNA clone (SEQ ID NO:1) encodes a 489 amino acid polypeptide (SEQ ID NO:2) that contains a putative signal peptide (SP) at amino acids 1-33, an integrin-like inserted domain (1-domain) at amino acids 44-214 and a type I transmembrane (TM) domain at amino acids 318-334 (FIG. 2). A BLAST search of the GenBank database revealed that the first 476 amino acids matched a protein (SEQ ID NO:4) encoded by an uncharacterized cDNA clone (SEQ ID NO:3) listed as GenBank accession number AK091721. The region encoding the last 13 amino acids of the cytoplasmic tail matched that of another CMG-2 cDNA clone (GenBank accession number AY040326). Presumably this difference between the cDNA clones is the result of alternative splicing of the primary CMG-2 mRNA transcript. The search also revealed that the isolated CMG-2 (SEQ ID NOS:1 and 2) was identical to the CMG-2 published by Bell et al. (2001) (SEQ ID NO:5 and SEQ ID NO:6) except for a 103 amino acid region (amino acids 213-315 of SEQ ID NO:2) not present in the Bell et al. (2001) CMG-2 protein. Neither of these previously identified CMG-2 clones and their proteins have heretofore been identified as a complete or partial anthrax toxin receptor.

Figure 4:
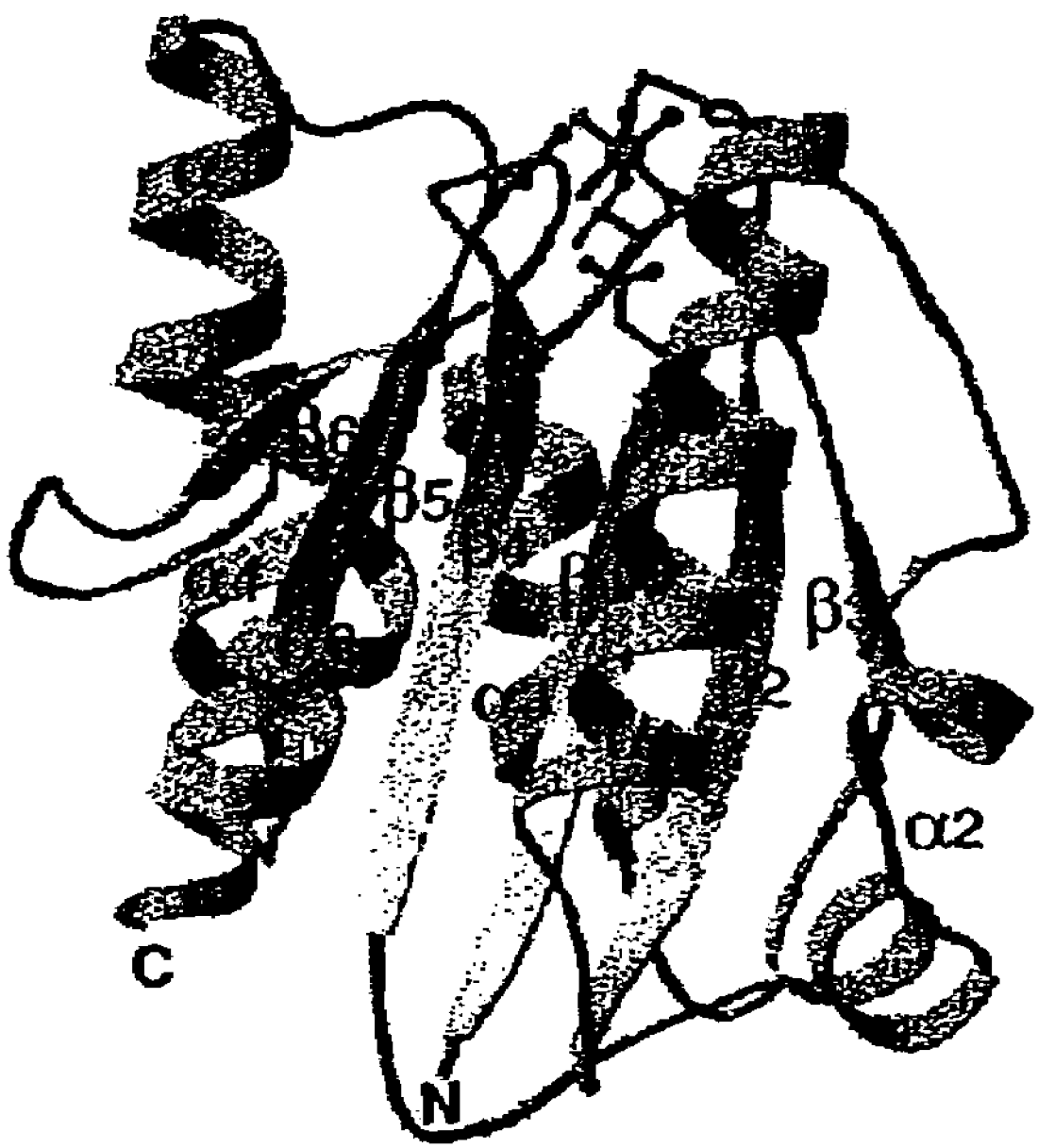
FIG. 4—An illustration of the oM I-domain.

As illustrated in FIG. 3, the I-domain of the CMG-2 protein is 56% identical to that of ATR/TEM8 (SEQ ID NO:8). Integrin I-domains are found in approximately one-half of all known integrin a-subunits and are the major ligand-binding region if present (Shimaoka et al., 2002). Integrin I-domains adopt the dinucleotide-binding (Rossmann) fold with a central β-sheet containing six β-strands surrounded by six major α-helices and other short α-helices (FIG. 4). Integrin I-domains also generally include a metal ion-dependent adhesion site (MIDAS), comprised of five amino acid residues (DX-SXS . . . T . . . D; where X can be any amino acid), present at the top of the integrin I-domain. The MIDAS motif and a bound divalent cation are generally important for ligand interaction as the ligand contributes a carboxylate side chain that acts as a sixth coordinating residue for the ion, thus greatly stabilizing the ligand-integrin interaction (Shimaoka et al., 2002). It is believed that the MIDAS motif of ATR (D50, S52, S54 . . . T118 . . . D150) and CMG-2 (D50, S52, S54 . . . T118 . . . D(148 or 152),) is critical for interaction with PA, and that such a motif may also be critical for other not yet identified anthrax toxin receptors.

An isolated polynucleotide and an isolated polypeptide, as used herein, can be isolated from its natural environment or synthesized. Complete purification is not required in either case. Amino acid and nucleotide sequences flanking an isolated polypeptide or polynucleotide occurring in nature can, but need not, be absent from the isolated form. Further, an isolated polynucleotide has a structure that is not identical to that of any naturally occurring nucleic acid or to that of any fragment of a naturally occurring genomic nucleic acid spanning more than three separate genes. The term includes, without limitation: (a) a nucleic acid molecule having a sequence of a naturally occurring genomic or extrachromosomal nucleic acid molecule but which is not flanked by the coding sequences that flank the sequence in its natural position; (b) a nucleic acid molecule incorporated into a vector or into a prokaryote or eukaryote genome such that the resulting molecule is not identical to any naturally occurring vector or genomic DNA; (c) a separate molecule such as a cDNA, a genomic fragment, a fragment produced by polymerase chain reaction (PCR™), or a restriction fragment; and (d) a recombinant nucleotide sequence that is part of a hybrid gene, i.e., a gene encoding a fusion protein. An isolated nucleic acid molecule can be modified or unmodified DNA or RNA, whether fully or partially single-stranded or double-stranded or even triple-stranded. A nucleic acid molecule may be chemically or enzymatically modified and may include so-called non-standard bases such as inosine.

In addition to the full-length and partial CMG-2 polypeptide sequences presented in SEQ ID NO:2, SEQ ID NO:4, and SEQ ID NO:6, other polypeptide fragments shorter than those sequences that retain PA-binding activity, and variants thereof, are also within the scope of the invention. The entire receptor is not required for utility; rather, fragments that bind to PA are useful in the invention.

A skilled artisan can readily assess whether a fragment binds to PA. A polypeptide is considered to bind to PA if the equilibrium dissociation constant of the binary complex is 10 micromolar or less. PA-binding to CMG-2 (or a fragment of CMG-2) can be measured using a protein-protein binding method such as coimmunoprecipitation, affinity column analysis, ELISA analysis, flow cytometry or fluorescence resonance energy transfer (FRET), and surface plasmon resonance (SPR). SPR is particularly suited as it is highly sensitive and accurate, operable in real time, and consumes only minute amounts of protein. SPR uses changes in refractive index to quantify macromolecular binding and dissociation to a ligand covalently tethered to a thin gold chip in a micro flow cell. Besides the equilibrium dissociation constant (Kd), on- and off-rate constants (ka and kd) can also be obtained. A BIAcore 2000 instrument (Pharmacia Biotech) can be used for these measurements. Typically, a protein is covalently tethered to a carboxymethyl dextran matrix bonded to the gold chip. Binding of a proteinaceous ligand to the immobilized protein results in a quantifiable change in refractive index of the dextran/protein layer. SPR can also be used to determine whether the interaction between PA and its receptor is sensitive to low pH, which is relevant to toxin endocytosis. This technique has been used to study protein-protein interactions in many systems, including the interactions of $PA_{63}$ with EF and LF.

The invention also relates to polypeptides that are at least 80%, preferably at least 90%, more preferably at least 95%, still more preferably at least 97%, or most preferably at least 99% identical to any aforementioned PA-binding polypeptide fragment, where PA-binding is maintained. As used herein, "percent identity" between amino acid or nucleic acid sequences is synonymous with "percent homology," which can be determined using the algorithm of Karlin and Altschul (1990), modified by Karlin and Altschul (1993). Such an algorithm is incorporated into the NBLAST and XBLAST programs of Altschul et al. (1990). BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference polypeptide (e.g., SEQ ID NO:2). To obtain gapped alignments for comparison purposes, Gapped BLAST is utilized as described in Altschul et al. (1997). When utilizing BLAST and Gapped BLAST programs, the default parameters of the respective programs (e.g., XBLAST and NBLAST) are used. See www.ncbi.nlm.nih.gov. A variant can also include, e.g., an internal deletion or insertion, a conservative or non-conservative substitution, or a combination of these variations from the sequence presented.

Soluble fragments are of great interest as these can competitively inhibit anthrax toxin binding to either CMG-2 or ATR and thereby protect cells from anthrax intoxication in vivo and in vitro. A fragment is soluble if it is not membrane-bound and is soluble in an aqueous fluid. The extracellular CMG-2 domain is a soluble fragment of the CMG-2, as are fragments of that domain. Even though the Integrin I-domain is formally identified as extending from amino acid 44 to 214 in the extracellular domain, more or fewer natively adjacent amino acids can be included in the fragment without compromising solubility or PA-binding. For example, a PA-binding fragment having the sequence of SEQ ID NO:2 or SEQ ID NO:4 beginning at any amino acid in the range from 33 to 43 and ending at any amino acid in the range from 214 to 489. A PA-binding fragment having the sequence of SEQ ID NO:6 beginning at any amino acid in the range from 33 to 43 and ending at any amino acid in the range from 212 to 386. A preferred soluble, PA-binding fragment extends from amino acid 44 to 214 of either SEQ ID NOS:2, 4 or 6. Another preferred soluble PA-binding fragment includes a fragment of CMG-2 from amino acid 33 through amino acid 214 of either SEQ ID NOS:2, 4 or 6. Likewise, any polypeptide fragment of these preferred fragments that retains PA-binding activity is within the scope of the invention. Preferably, such fragments include the MIDAS motif comprised of five amino acid residues (DXSXS . . . T . . . D; where X can be any amino acid). CMG-2 in soluble form is effective in a monomeric form, as well as in multimeric forms such as dimeric, tetrameric, pentameric and higher oligomeric forms.

PA-binding polypeptides can include, therefore, SEQ ID NO:2, SEQ ID NO:4, SEQ ID NO:6, a PA-binding fragment of SEQ ID NO:2, a PA-binding fragment of SEQ ID NO:4, a PA-binding fragment of SEQ ID NO:6, a PA-binding polypeptide at least 80% identical to any of the foregoing fragments. The PA-binding polypeptides can also be provided as fusion proteins comprising any of the foregoing that can comprise still other non-natively adjacent amino acids for detecting, visualizing, isolating, or stabilizing the polypeptide. For example, PA binds to the fusion protein of EGFP (enhanced green fusion protein) fused to the C-terminal residue of the cytoplasmic tail of the CMG-2 cDNA clone.

Likewise, isolated polynucleotides having an uninterrupted nucleic acid sequence encoding any of the aforementioned polypeptides and polypeptide fragments may be used to practice the present invention. The sequences that encode soluble, PA-binding polypeptide fragments of CMG-2 are immediately apparent to the skilled artisan from the description of the relevant portions of the polypeptides, supra. An isolated nucleic acid containing the complement of any such polynucleotides, when used to generate or develop anthrax antitoxins, is also within the scope of the present invention, as are polynucleotide and oligonucleotide fragments for use as molecular probes.

The present invention also relates to an isolated polynucleotide and its complement, without regard to source, where the polynucleotide hybridizes under stringent or moderately stringent hybridization conditions to SEQ ID NO: 1, SEQ ID NO:3, or SEQ ID NO:5, or to a fragment of any of the foregoing that encodes a soluble polypeptide that binds to PA. Such a polypeptide can not include SEQ ID NO:3 or SEQ ID NO:5. As used herein, stringent conditions involve hybridizing at 68° C. in 5×SSC/5×Denhardt's solution/1.0% SDS, and washing in 0.2×SSC/0.1% SDS +/−100 µg/ml denatured salmon sperm DNA, at room temperature. Moderately stringent conditions include washing in the same buffer at 42° C. Additional guidance regarding such conditions is readily available in the art, for example, by Sambrook et al. (2001); Ausubel et al. (1996).

In a related aspect, any polynucleotide used to practice the present invention can be provided in a vector in a manner known to those skilled in the art. The vector can be a cloning vector or an expression vector. In an expression vector, the polypeptide-encoding polynucleotide is under the transcriptional control of one or more non-native expression control sequences, such as a promoter not natively adjacent to the polynucleotide, such that the encoded polypeptide can be produced when the vector is delivered into a compatible host cell that supports expression of an polypeptide encoded on a vector, for example by electroporation or transfection, or transcribed and translated in a cell-free transcription and translation system. Such cell-based and cell-free systems are well known to the skilled artisan. Cells comprising an insert-containing vector of the invention are themselves within the scope of the present invention, without regard to whether the vector is extrachromosomal or integrated in the genome.

A skilled artisan in possession of the polypeptides and polynucleotides of the invention can also identify agents that can reduce or prevent the effect of anithrax toxin on a host having on the cell surface at least a portion of a receptor that binds PA. The effect altered can relate, for example, to (1) susceptibility of the host cell to anthrax toxin damage, (2) integration of CMG-2, ATR or PA into the cell membrane, (3) binding between PA and CMG-2 or ATR, (4) PA heptamerization, (5) uptake of the PA/CMG-2 complex or the PA/ATR complex into cells, and (6) the translocation of toxin into host cell cytoplasm. The method includes separately exposing a plurality of putative agents in the presence of anthrax toxin to a plurality of cells, comparing the effect of anthrax toxin on the cells in the presence and absence of the agent, and identifying at least one agent that alters an effect of anthrax toxin on the cells.

The skilled artisan can readily evaluate the typical effects of anthrax toxin and observe variations in those effects in the presence of a putative altering agent. For example, susceptibility to anthrax toxin damage can be evaluated by exposing host cells to anthrax toxin. Integration of newly formed CMG-2 into the host cell membrane can be evaluated by labeling newly synthesized proteins in the host cell and immunoprecipitating CMG-2 from the cellular membrane fraction of the host cell. Binding of wild-type CMG-2 to PA can be evaluated with fluorescent labeled anti-PA antibody. PA heptamerization can be evaluated by several techniques including native polyacrylamide gel electrophoresis, gel filtration, and western blotting. Uptake of PA/ATR or PA/CMG-2 complex can be evaluated by binding PA to ATR or CMG-2 at 4° C., increasing the temperature to 37° C. to allow endocytosis, shifting the temperature back to 4° C., and incubating cells with fluorescent labeled anti-PA antibodies. Toxin translocation into the host cell cytoplasm can be evaluated as described in Wesche et al. (1998), which is incorporated herein by reference as if set forth in its entirety.

The agents screened can be, for example, a high molecular weight molecule such as a polypeptide (including, e.g., a mutant anthrax toxin, a soluble CMG-2, a monoclonal or polyclonal antibody to CMG-2; PA, or an PA/CMG-2 complex), a polysaccharide, a lipid, a nucleic acid, a low molecular weight organic or inorganic molecule, or the like. Antibodies can be produced by administering to a non-human animal an immunogenic, PA-binding fragment of a polypeptide which can be, e.g., SEQ ID NO:2, SEQ ID NO:4, SEQ ID NO:6, a polypeptide at least 80% identical to any of the foregoing and a fusion protein comprising any of the foregoing, and then obtaining the desired antibodies using known methods.

Chemical libraries for screening putative agents, including peptide libraries, are readily available to the skilled artisan. Examples include those from ASINEX (i.e. the Combined Wisdom Library of 24,000 manually synthesized organic molecules) and from CHEMBRIDGE CORPORATION (i.e., the DIVERSet™ library of 50,000 manually synthesized chemical compounds; the SCREEN-Set™ library of 24,000 manually synthesized chemical compounds; the CNS-Set™ library of 11,000 compounds; the Cherry-Pick™ library of up to 300,000 compounds) and linear library, multimeric library and cyclic library (Tecnogen, Italy). Once an agent with desired activity is identified, a library of derivatives of that agent can be screened for better agents. Phage display is also a suitable approach for finding novel inhibitors of the interaction between PA and both CMG-2 and ATR.

Another aspect of the present invention relates to CMG-2 ligands other than PA, laminine and collagen type IV, and methods for identifying such other ligands. To identify these other ligands, a polypeptide that contains a CMG-2 Integrin I-domain, preferably an entire extracellular domain, can be provided in soluble or tethered form, e.g., in a chromatographic column. Preferably, the I-domain of CMG-2 can be provided as a fusion protein that also contains rabbit IgG constant region, a GST domain or a hexahistidine tag. This fusion protein can be immobilized on a chromatographic column using known methods. A cell extract can be passed over the column. A ligand is identified when binding is observed between the I-domain and a compound present in the cell extract. The identified ligand can be used in methods for identifying agents that alter an effect of anthrax toxin, to identify an agent that selectively inhibits PA-receptor binding. It is also desirable to use the other ligands and CMG-2 in comparative high throughput screening methods for identifying small molecules that do not interfere with natural ligand binding to CMG-2, but which do prevent or reduce binding of CMG-2 or other receptors to anthrax toxin.

The present invention also relates to reducing cellular damage caused by anthrax toxin, which can be achieved by administering an agent for reducing CMG-2 levels, inhibiting the binding between CMG-2 and PA, or by reducing downstream CMG-2 activity after binding to PA. For example, an antisense oligonucleotide can reduce or prevent expression of CMG-2 using delivery methods known to the skilled artisan, thus reducing the cellular CMG-2 level. A CMG-2 anthrax binding inhibition agent can competitively inhibit the binding between CMG-2 and PA and/or PA and other anthrax toxin receptors, such as ATR. Dominant negative CMG-2s can block downstream CMG-2 activities required for anthrax toxin toxicity. Such agents can be administered to a human or non-human animal, preferably in a standard pharmaceutical carrier, in an amount effective to reduce or eliminate anthrax toxicity.

A 20-25 mer antisense oligonucleotide can be directed against the 5' end of CMG-2 mRNA with phosphorothioate derivatives on the last three base pairs on the 3' end and the 5' end to enhance the half life and stability of the oligonucleotides. A carrier for an antisense oligonucleotide can be used. An example of a suitable carver is cationic liposomes. For example, an oligonucleotide can be mixed with cationic liposomes prepared by mixing 1-alpha dioleylphatidylcelthanolamine with dimethldioctadecylammomum bromide in a ratio of 5:2 in 1 ml of chloroform. The solvent will be evaporated and the lipids resuspended by sonication in 10 ml of saline.

Another way to use an antisense oligonucleotide is to engineer it into a vector so that the vector can produce an antisense cRNA that blocks the translation of the mRNAs encoding for CMG-2. Similarly, RNAi techniques, which are now being applied to mammalian systems, are also suited for inhibiting CMG-2 expression. (Zamore, 2001, incorporated herein by reference as if set forth in its entirety).

The present invention also relates to a method for detecting CMG-2 mRNA or CMG-2 protein in a sample. Such detection can be readily accomplished by using oligonucleotide or polynucleotide probes for CMG-2 mRNA, or antibodies for the CMG-2 protein. In a related aspect, the antibodies made and identified as being able to bind to CMG-2 can also be used to separate CMG-2 from a sample.

The invention also relates to the use of cell lines containing or not containing CMG-2 for testing anthrax toxicity, and methods for making such cell lines. Methods for developing such cell lines are well known by the skilled artisan. For example, generating a cell line that does not express CMG-2 may be feasible using mutagenesis and screening, or homologous recombination. Such cell lines and their use are deemed to be within the scope of the present invention.

The invention also provides molecules and methods for specifically targeting and killing cells of interest by delivering, e.g., anthrax toxin or LF to the cell. It is anticipated that soluble CMG-2 molecules can be coupled to a ligand or to a single chain antibody selected for targeting to the cell of interest (e.g., a ligand that binds a receptor presented on a tumor cell surface). The coupling may be accomplished by producing a fusion protein that encodes both the CMG-2 binding portion and the ligand or single chain antibody molecule. The ligand or single chain antibody domains simply serve to attach the toxin to cells with the cognate surface markers. The toxin or factor may be preloaded onto the CMG-2 portion before exposing the coupled molecules to the targeted cells. This is similar in principle to that previously described for retroviral targeting using soluble retroviral receptor-ligand bridge proteins and retroviral receptor-single chain antibody bridge proteins (Snitkovsky and Young, 1998; Boerger et al., 1999; Snitkovsky et al., 2000; Snitkovsky et al., 2001), each incorporated herein by reference as if set forth in its entirety.

The invention will be more fully understood upon consideration of the following non-limiting examples.

EXAMPLE 1

Figure 5:
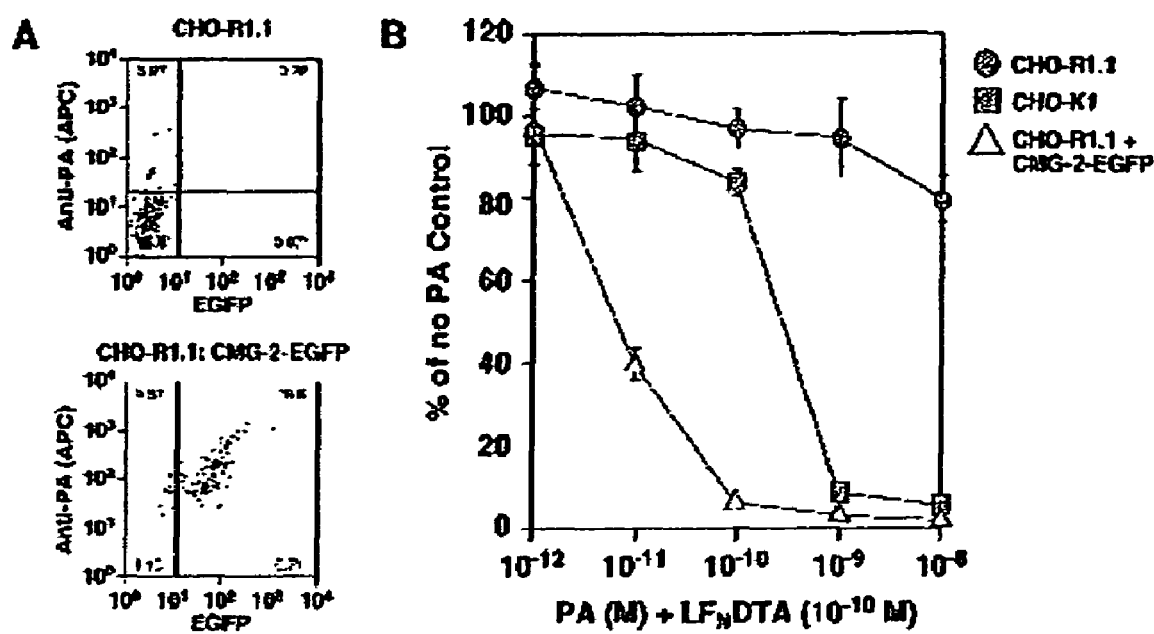
FIG. 5—A graphic illustration of the functionality of CMG-2 as an anthrax toxin receptor.

To test CMG-2 function and to facilitate protein detection, a fusion protein was generated in which EGFP was fused to the C-terminal residue of the cytoplasmic tail of the HS003 CMG-2 cDNA clone (SEQ ID NO:1). This strategy was used because it had previously been shown that a similarly constructed ATR-EGFP fusion protein was competent for PA-binding and intoxication. The gene encoding CMG-2-EGFP was expressed from a retroviral vector in CHO-R1.1 cells that lack anthrax toxin receptors as described in Bradley et al., supra, incorporated herein by reference. These cells bound PA (FIG. 5A) and were highly susceptible to cell killing by PA and LFn-DTA (FIG. 5B). Therefore, CMG-2 is a bona fide anthrax toxin receptor.

EXAMPLE 2

CMG2-488 (Genbank Accession No. AK091721) is different from CMG2-489 (Genbank Accession No. AY233452) in its C-terminal 12 amino acids. Although CMG-489 is only one amino longer in total length, the C-terminal 13 amino acids of CMG2-489 have been replaced with 12 different amino acids that are derived from the C-terminus of CMG2-488. Both of these CMG2 protein isoforms are encoded by naturally occurring mRNA splice variants. CMG2-488 has been shown by RT-PCR analysis to be expressed in most tissues (15 of 16 human tissues tested). Since CMG2-488 can act as a toxin receptor, this broad expression makes it likely to play a role in in vivo anthrax intoxication.

Figure 6:
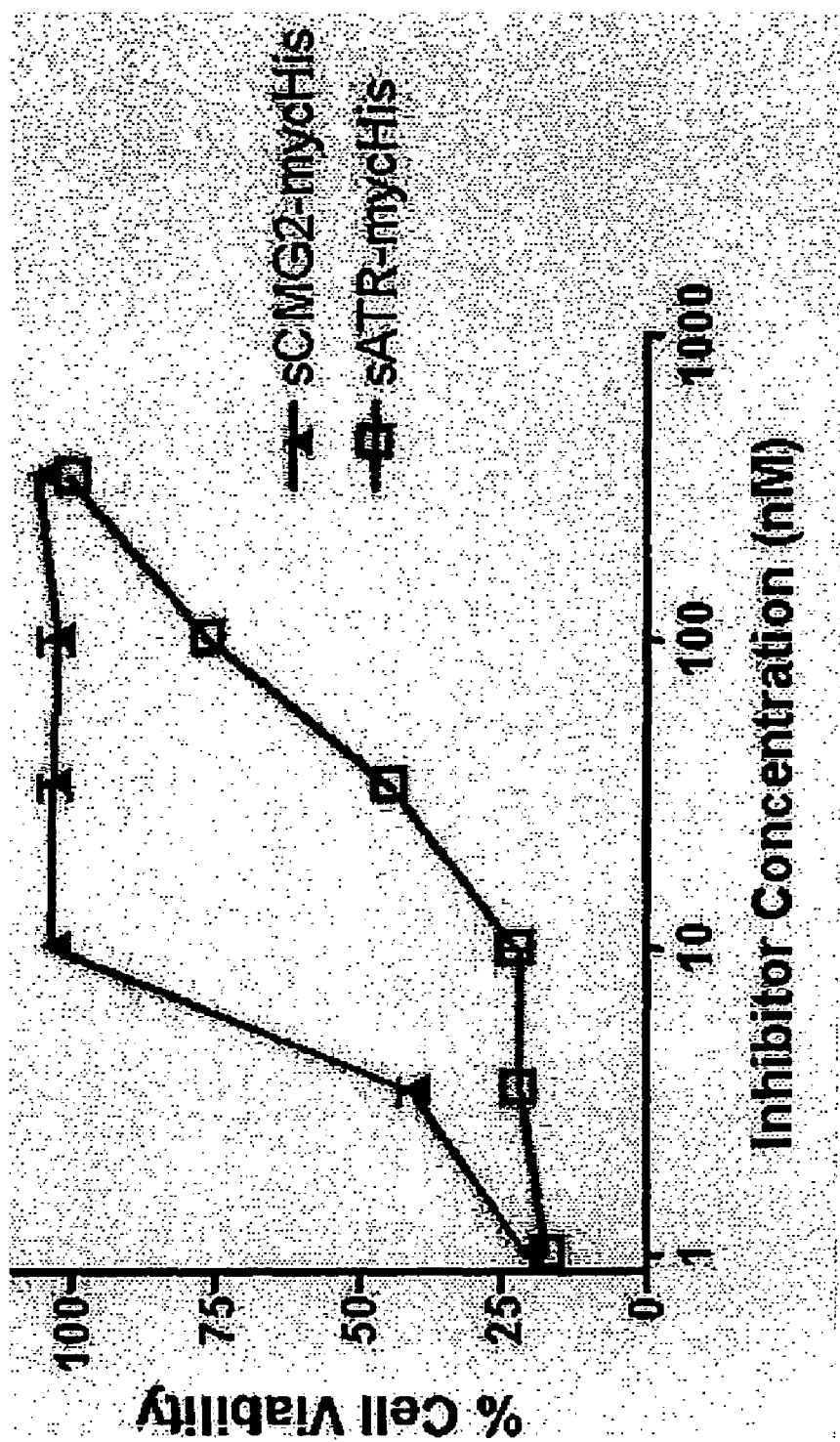
FIG. 6—Soluble CMG2I domaing (sCMG2) inhibits CHO-K1 cell intoxication with 10-fold greater potency than soluble ATR I domain (sATR). Five thousand CHO-K1 cells were incubated with $10^{-10}$ M LFn-DTA and $10^{-9}$ PA for 30 hr in the presence of varying amounts of mammalian cell produced and nickel affinity purified sATR-mycHis or sCMG2-mycHis proteins (sequences encoding residues 1-234 (Bradley et al., 2001) or 1-232 (Scobie et al., 2003), respectively, cloned in frame with a myc epitope and six histidine tag in the pcDNA3.1/mycHis(−)A vector (Invitrogen)). After incubation, cell viability was measured with the Wst-1 assay (Roche) and expressed as a percentage of the viability of samples incubated with no PA (100% viable).

When similarly constructed and produced soluble ATR and CMG2 I domain proteins (sATR and sCMG2 respectively) were tested as inhibitors (receptor decoys) of intoxication in a cell culture model, sCMG2 was 10-fold more potent than sATR in protecting cultured cells from death (FIG. 6). This may indicate that the CMG2-PA binding interaction is stronger than that of ATR-PA, but this remains to be formally proven in binding affinity studies. Nevertheless, this difference in relative potency suggests that sCMG2 is a better candidate for use as an in vivo receptor-based antitoxin.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Altschul et al., *Nucleic Acids Res.*, 25:3389-3402, 1997.
Altschul et al., *J. Mol. Biol.*, 215:403-410, 1990.
Ausubel et al., In: *Current Protocols in Molecular Biology*, John, Wiley & Sons, Inc, New York, 1996.
Bell et al., *J. Cell Science*, 113:2755-2773, 2001.
Benson et al., *Biochem.*, 37:3941-3948, 1998.
Boerger et al., *Proc. Natl. Acad. Sci.* USA, 96:9687-9872, 1999.
Bradley et al., *Nature*, 414:225-229, 2001.
Cunningham et al., *Proc. Natl. Acad. Sci.* USA, 99:7049-7053, 2002.
Friedlander et al., *JAMA*, 282:2104-2106, 1999.
Inglesby et al., *JAMA*, 287:2236-2252, 2002.
Karlin and Altschul, *Proc. Natl. Acad. Sci.* USA, 87:2264-2268, 1990.
Karlin and Altschul, *Proc. Natl. Acad. Sci.* USA, 90:5873-5877, 1993.
Maynard et al., *Nature Biotech.*, 20:597-601, 2002.
Mock and Fouet, *Annual Rev. Microbiology*, 55:647-671, 2001.
Mogridge et al., *Proc. Natl. Acad. Sci.* USA, 99:7045-7048, 2002.
Mourez et al., *Nature Biotech.*, 19:958-961, 2001.
Petosa et al., *Nature*, 385:833-838, 1997.
Sambrook et al., In: *Molecular cloning*, Cold Spring Harbor Laboratory Press, Cold Spring Harbor, N.Y., 2001.

Schuch et al., *Nature*, 418:884-889, 2002.

Scobie et al., *Proc. Natl. Acad. Sci.* USA, 100(9) 5170-74, 2003.

Sellman et al., *Science*, 292:695-697, 2001.

Shimaoka et al., *Annual Rev. Biophysics Biomolec. Struct*, 31:486-516, 2002.

Snitkovsky and Young, *Proc. Natl. Acad. Sci.* USA, 95:7063-7068, 1998.

Snitkovsky et al., *J. Virol.*, 74:9540-9545, 2000.

Snitkovsky et al., *J. Virol.*, 75:1571-1575, 2001.

Vastag, *JAMA*, 287:1516-1517, 2002.

Wesche et al., *Biochemistry*, 37(45):15737-15746, 1998.

Zamore, *Nat. Struct. Biol.*, 8:746-750, 2001.

---

What is claimed:

1. A method comprising the step of administering to a human or non-human animal infected by or exposed to anthrax a polypeptide that inhibits binding between protective antigen (PA) and human capillary morphogenesis protein-2 (CMG-2) at a level effective to reduce the severity of anthrax infection, wherein said polypeptide comprises residues 44-214 of SEQ ID NO:2 or residues 44-317 of SEQ ID NO:2.

2. The method of claim 1, wherein said human or non-human animal has an anthrax infection.

* * * * *